(12) United States Patent
Yang et al.

(10) Patent No.: US 10,106,609 B2
(45) Date of Patent: Oct. 23, 2018

(54) CD7 NANOBODIES, ENCODING SEQUENCE AND USE THEREOF

(71) Applicant: PersonGen BioTherapeutics (Suzhou) Co., Ltd., Jiangsu (CN)

(72) Inventors: Lin Yang, Jiangsu (CN); Jinle Tang, Jiangsu (CN)

(73) Assignee: PeronGen BioTherapeutics (Suzhou) Co., Ltd., Suzhou, Jiangsu (CN)

( * ) Notice: Subject to any disclaimer, the term of this patent is extended or adjusted under 35 U.S.C. 154(b) by 0 days.

(21) Appl. No.: 15/316,256

(22) PCT Filed: Apr. 29, 2015

(86) PCT No.: PCT/CN2015/077854
§ 371 (c)(1),
(2) Date: Apr. 21, 2017

(87) PCT Pub. No.: WO2015/184941
PCT Pub. Date: Dec. 10, 2015

(65) Prior Publication Data
US 2017/0226204 A1 Aug. 10, 2017

(30) Foreign Application Priority Data
Jun. 4, 2014 (CN) .......................... 2014 1 0244584

(51) Int. Cl.
*C07K 16/28* (2006.01)
*G01N 33/68* (2006.01)
*C07K 14/21* (2006.01)
*A61K 39/00* (2006.01)

(52) U.S. Cl.
CPC .......... *C07K 16/2803* (2013.01); *C07K 14/21* (2013.01); *G01N 33/6872* (2013.01); *A61K 2039/505* (2013.01); *C07K 2317/35* (2013.01); *C07K 2317/569* (2013.01); *C07K 2317/92* (2013.01); *C07K 2319/55* (2013.01); *G01N 2333/70503* (2013.01)

(58) Field of Classification Search
CPC .......... C07K 16/2803; C07K 2317/569; C07K 2317/35; G01N 2333/70503
USPC ........................................... 424/133.1, 178.1
See application file for complete search history.

(56) References Cited

FOREIGN PATENT DOCUMENTS

| CN | 102812042 | 12/2012 |
| CN | 104004095 | 8/2014 |
| WO | 2011095506 A1 * | 8/2011 |
| WO | 2017025038 A1 * | 2/2017 |

OTHER PUBLICATIONS

Tang et al. (Oncotarget, vol. 7, No. 23: 34070-34083 (Apr. 2016)).*
Yu et al. (International Journal of Nanomedicine 2017:12 1969-1983).*
Yu et al. (Haematologica, (Jun. 2017) vol. 102, Supp. Supplement 2, pp. 448-449. Abstract No. E1087).*
International Search Report for international application No. PCT/CN2015/077854, dated Jun. 12, 2015 (4 pages, including English translation).

* cited by examiner

*Primary Examiner* — Lynn A Bristol
(74) *Attorney, Agent, or Firm* — Hamre, Schumann, Mueller & Larson, P.C.

(57) ABSTRACT

Provided is a nanometer antibody for human CD7 molecule and an encoding DNA sequence thereof. The nanometer antibody can be efficiently expressed in *Escherichia coli*, and can be used for preparing an agent for the detection of CD7 molecule and targeted therapy.

10 Claims, 10 Drawing Sheets
Specification includes a Sequence Listing.

SEQUENCE LISTING

```
<160> NUMBER OF SEQ ID NOS: 51

<210> SEQ ID NO 1
<211> LENGTH: 26
<212> TYPE: PRT
<213> ORGANISM: artificial sequence
<220> FEATURE:
<223> OTHER INFORMATION: Polypeptide

<400> SEQUENCE: 1

Met Asp Val Gln Leu Gln Glu Ser Gly Gly Gly Ser Val Gln Ala Gly
1               5                   10                  15

Gly Ser Leu Arg Leu Ser Cys Pro Ala Ser
            20                  25

<210> SEQ ID NO 2
<211> LENGTH: 15
<212> TYPE: PRT
<213> ORGANISM: artificial sequence
<220> FEATURE:
<223> OTHER INFORMATION: Polypeptide

<400> SEQUENCE: 2

Gly Trp Asn Arg Gln Ala Pro Gly Lys Glu Arg Glu Val Ala
1               5                   10                  15

<210> SEQ ID NO 3
<211> LENGTH: 37
<212> TYPE: PRT
<213> ORGANISM: artificial sequence
<220> FEATURE:
<223> OTHER INFORMATION: Polypeptide

<400> SEQUENCE: 3

Tyr Ala Asp Ser Val Met Gly Arg Phe Thr Ile Ser Arg Asp Asn Ala
1               5                   10                  15

Asn Asn Ala Leu Tyr Leu Gln Met Asn Asp Leu Lys Pro Glu Asp Thr
            20                  25                  30

Ser Met Tyr Tyr Cys
        35
```

```
<210> SEQ ID NO 4
<211> LENGTH: 11
<212> TYPE: PRT
<213> ORGANISM: artificial sequence
<220> FEATURE:
<223> OTHER INFORMATION: Polypeptide

<400> SEQUENCE: 4

Gly Gln Gly Thr Gln Val Thr Val Ser Ile Asn
1               5                   10

<210> SEQ ID NO 5
<211> LENGTH: 26
<212> TYPE: PRT
<213> ORGANISM: artificial sequence
<220> FEATURE:
<223> OTHER INFORMATION: Polypeptide

<400> SEQUENCE: 5

Met Asp Val Gln Leu Gln Glu Ser Gly Gly Gly Ser Val Gln Ala Gly
1               5                   10                  15

Gly Ser Leu Arg Leu Ser Cys Ala Ala Ser
            20                  25

<210> SEQ ID NO 6
<211> LENGTH: 15
<212> TYPE: PRT
<213> ORGANISM: artificial sequence
<220> FEATURE:
<223> OTHER INFORMATION: Polypeptide

<400> SEQUENCE: 6

Ala Trp Phe Arg Gln Ala Pro Gly Arg Glu Arg Glu Gly Val Ala
1               5                   10                  15

<210> SEQ ID NO 7
<211> LENGTH: 37
<212> TYPE: PRT
<213> ORGANISM: artificial sequence
<220> FEATURE:
<223> OTHER INFORMATION: Polypeptide

<400> SEQUENCE: 7

Tyr Ala Asp Ser Val Lys Gly Arg Phe Thr Ile Ser Gln Asp Asn Ala
1               5                   10                  15

Lys Asn Thr Leu Tyr Leu Gln Met Asn Ser Leu Lys Pro Glu Asp Thr
            20                  25                  30

Ala Met Tyr Tyr Cys
        35

<210> SEQ ID NO 8
<211> LENGTH: 12
<212> TYPE: PRT
<213> ORGANISM: artificial sequence
<220> FEATURE:
<223> OTHER INFORMATION: Polypeptide

<400> SEQUENCE: 8

Trp Gly Gln Gly Thr Gln Val Thr Val Ser Ile Thr
1               5                   10

<210> SEQ ID NO 9
<211> LENGTH: 15
<212> TYPE: PRT
<213> ORGANISM: artificial sequence
```

<220> FEATURE:
<223> OTHER INFORMATION: Polypeptide

<400> SEQUENCE: 9

Gly Trp Leu Arg Gln Ala Pro Gly Lys Glu Arg Glu Val Ala
1               5                   10                  15

<210> SEQ ID NO 10
<211> LENGTH: 15
<212> TYPE: PRT
<213> ORGANISM: artificial sequence
<220> FEATURE:
<223> OTHER INFORMATION: Polypeptide

<400> SEQUENCE: 10

Ala Trp Phe Arg Gln Phe Pro Gly Lys Glu Arg Glu Gly Val Ala
1               5                   10                  15

<210> SEQ ID NO 11
<211> LENGTH: 37
<212> TYPE: PRT
<213> ORGANISM: artificial sequence
<220> FEATURE:
<223> OTHER INFORMATION: Polypeptide

<400> SEQUENCE: 11

Tyr Ala Asp Ser Val Lys Gly Arg Phe Thr Leu Ser Glu Asp Ser Ala
1               5                   10                  15

Lys Asn Thr Val Tyr Leu Glu Met Asn Ser Leu Gln Pro Glu Asp Thr
                20                  25                  30

Ala Met Tyr Tyr Cys
            35

<210> SEQ ID NO 12
<211> LENGTH: 12
<212> TYPE: PRT
<213> ORGANISM: artificial sequence
<220> FEATURE:
<223> OTHER INFORMATION: Polypeptide

<400> SEQUENCE: 12

Trp Gly Gln Gly Thr Gln Val Thr Val Ser Ile Asn
1               5                   10

<210> SEQ ID NO 13
<211> LENGTH: 26
<212> TYPE: PRT
<213> ORGANISM: artificial sequence
<220> FEATURE:
<223> OTHER INFORMATION: Polypeptide

<400> SEQUENCE: 13

Met Asp Val Gln Leu Gln Glu Ser Gly Gly Gly Leu Val Gln Ala Gly
1               5                   10                  15

Gly Ser Leu Arg Leu Ser Cys Ala Val Ser
                20                  25

<210> SEQ ID NO 14
<211> LENGTH: 15
<212> TYPE: PRT
<213> ORGANISM: artificial sequence
<220> FEATURE:
<223> OTHER INFORMATION: Polypeptide

<400> SEQUENCE: 14

```
Gly Trp Phe Arg Gln Ala Pro Gly Lys Glu Arg Glu Gly Val Ala
1               5                   10                  15
```

```
<210> SEQ ID NO 15
<211> LENGTH: 37
<212> TYPE: PRT
<213> ORGANISM: artificial sequence
<220> FEATURE:
<223> OTHER INFORMATION: Polypeptide

<400> SEQUENCE: 15

Tyr Ala Asp Ser Val Lys Gly Arg Phe Thr Ile Ser Gln Asp Asn Ala
1               5                   10                  15

Lys Asn Thr Leu Tyr Leu Gln Met Asn Arg Met Lys Pro Glu Asp Thr
            20                  25                  30

Ala Met Tyr Tyr Cys
        35
```

```
<210> SEQ ID NO 16
<211> LENGTH: 37
<212> TYPE: PRT
<213> ORGANISM: artificial sequence
<220> FEATURE:
<223> OTHER INFORMATION: Polypeptide

<400> SEQUENCE: 16

Tyr Ala Asp Ser Val Lys Gly Arg Phe Thr Ile Ser Arg Asp Asn Ala
1               5                   10                  15

Lys Asn Thr Leu Asn Leu Gln Met Ser Ser Leu Lys Pro Glu Asp Thr
            20                  25                  30

Ala Met Tyr Tyr Cys
        35
```

```
<210> SEQ ID NO 17
<211> LENGTH: 9
<212> TYPE: PRT
<213> ORGANISM: artificial sequence
<220> FEATURE:
<223> OTHER INFORMATION: Polypeptide

<400> SEQUENCE: 17

Gly Tyr Thr Phe Ser His Tyr Cys Met
1               5
```

```
<210> SEQ ID NO 18
<211> LENGTH: 9
<212> TYPE: PRT
<213> ORGANISM: artificial sequence
<220> FEATURE:
<223> OTHER INFORMATION: Polypeptide

<400> SEQUENCE: 18

Thr Ile Asp Thr Asp Asp Thr Pro Thr
1               5
```

```
<210> SEQ ID NO 19
<211> LENGTH: 18
<212> TYPE: PRT
<213> ORGANISM: artificial sequence
<220> FEATURE:
<223> OTHER INFORMATION: Polypeptide

<400> SEQUENCE: 19

Ala Ile Trp Met Lys Leu Arg Gly Ser Cys His Asp Arg Arg Leu Glu
1               5                   10                  15
```

Val Arg

<210> SEQ ID NO 20
<211> LENGTH: 9
<212> TYPE: PRT
<213> ORGANISM: artificial sequence
<220> FEATURE:
<223> OTHER INFORMATION: Polypeptide

<400> SEQUENCE: 20

Gly Tyr Thr His Ser Ser Tyr Cys Met
1               5

<210> SEQ ID NO 21
<211> LENGTH: 9
<212> TYPE: PRT
<213> ORGANISM: artificial sequence
<220> FEATURE:
<223> OTHER INFORMATION: Polypeptide

<400> SEQUENCE: 21

Ser Ile Asp Ser Asp Gly Thr Thr Ser
1               5

<210> SEQ ID NO 22
<211> LENGTH: 19
<212> TYPE: PRT
<213> ORGANISM: artificial sequence
<220> FEATURE:
<223> OTHER INFORMATION: Polypeptide

<400> SEQUENCE: 22

Ala Ala Arg Phe Gly Pro Met Gly Cys Val Asp Leu Ser Thr Leu Ser
1               5                   10                  15

Phe Gly His

<210> SEQ ID NO 23
<211> LENGTH: 9
<212> TYPE: PRT
<213> ORGANISM: artificial sequence
<220> FEATURE:
<223> OTHER INFORMATION: Polypeptide

<400> SEQUENCE: 23

Thr Ile Asp Thr Asp Ser Thr Pro Thr
1               5

<210> SEQ ID NO 24
<211> LENGTH: 18
<212> TYPE: PRT
<213> ORGANISM: artificial sequence
<220> FEATURE:
<223> OTHER INFORMATION: Polypeptide

<400> SEQUENCE: 24

Ala Thr Trp Met Gly Leu Arg Gly Ser Cys His Asp Arg Arg Leu Glu
1               5                   10                  15

Val Arg

<210> SEQ ID NO 25
<211> LENGTH: 9
<212> TYPE: PRT
<213> ORGANISM: artificial sequence
<220> FEATURE:
<223> OTHER INFORMATION: Polypeptide

<400> SEQUENCE: 25

Gly Tyr Thr Thr Ser Arg Leu Cys Met
1               5

<210> SEQ ID NO 26
<211> LENGTH: 10
<212> TYPE: PRT
<213> ORGANISM: artificial sequence
<220> FEATURE:
<223> OTHER INFORMATION: Polypeptide

<400> SEQUENCE: 26

Asn Val Arg Leu Gly Gly Tyr Lys Pro Ala
1               5                   10

<210> SEQ ID NO 27
<211> LENGTH: 21
<212> TYPE: PRT
<213> ORGANISM: artificial sequence
<220> FEATURE:
<223> OTHER INFORMATION: Polypeptide

<400> SEQUENCE: 27

Ala Ala Asp Pro Gly Gly Gly Ser Cys Pro Val Ala Leu Val Arg
1               5                   10                  15

Gly Asp Phe Asp Tyr
            20

<210> SEQ ID NO 28
<211> LENGTH: 9
<212> TYPE: PRT
<213> ORGANISM: artificial sequence
<220> FEATURE:
<223> OTHER INFORMATION: Polypeptide

<400> SEQUENCE: 28

Gly Tyr Pro Tyr Ser Ser Tyr Cys Met
1               5

<210> SEQ ID NO 29
<211> LENGTH: 9
<212> TYPE: PRT
<213> ORGANISM: artificial sequence
<220> FEATURE:
<223> OTHER INFORMATION: Polypeptide

<400> SEQUENCE: 29

Ala Ile Asp Ser Asp Gly Arg Thr Arg
1               5

<210> SEQ ID NO 30
<211> LENGTH: 9
<212> TYPE: PRT
<213> ORGANISM: artificial sequence
<220> FEATURE:
<223> OTHER INFORMATION: Polypeptide

<400> SEQUENCE: 30

Gly Tyr Thr Tyr Ser Thr Tyr Cys Met
1               5

<210> SEQ ID NO 31
<211> LENGTH: 9
<212> TYPE: PRT
<213> ORGANISM: artificial sequence
<220> FEATURE:
<223> OTHER INFORMATION: Polypeptide

<400> SEQUENCE: 31

Thr Ile Asp Ser Asp Gly Ser Thr Ser
1               5

<210> SEQ ID NO 32
<211> LENGTH: 125
<212> TYPE: PRT
<213> ORGANISM: artificial sequence
<220> FEATURE:
<223> OTHER INFORMATION: Polypeptide

<400> SEQUENCE: 32

Met Asp Val Gln Leu Gln Glu Ser Gly Gly Gly Ser Val Gln Ala Gly
1               5                   10                  15

Gly Ser Leu Arg Leu Ser Cys Pro Ala Ser Gly Tyr Thr Phe Ser His
                20                  25                  30

Tyr Cys Met Gly Trp Asn Arg Gln Ala Pro Gly Lys Glu Arg Glu Glu
            35                  40                  45

Val Ala Thr Ile Asp Thr Asp Asp Thr Pro Thr Tyr Ala Asp Ser Val
        50                  55                  60

Met Gly Arg Phe Thr Ile Ser Arg Asp Asn Ala Asn Asn Ala Leu Tyr
65                  70                  75                  80

Leu Gln Met Asn Asp Leu Lys Pro Glu Asp Thr Ser Met Tyr Tyr Cys
                85                  90                  95

Ala Ile Trp Met Lys Leu Arg Gly Ser Cys His Asp Arg Arg Leu Glu
            100                 105                 110

Val Arg Gly Gln Gly Thr Gln Val Thr Val Ser Ile Asn
        115                 120                 125

<210> SEQ ID NO 33
<211> LENGTH: 127
<212> TYPE: PRT
<213> ORGANISM: artificial sequence
<220> FEATURE:
<223> OTHER INFORMATION: Polypeptide

<400> SEQUENCE: 33

Met Asp Val Gln Leu Gln Glu Ser Gly Gly Gly Ser Val Gln Ala Gly
1               5                   10                  15

Gly Ser Leu Arg Leu Ser Cys Ala Ala Ser Gly Tyr Thr His Ser Ser
                20                  25                  30

Tyr Cys Met Ala Trp Phe Arg Gln Ala Pro Gly Arg Glu Arg Glu Gly
            35                  40                  45

Val Ala Ser Ile Asp Ser Asp Gly Thr Thr Ser Tyr Ala Asp Ser Val
        50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Arg Phe Gly Pro Met Gly Cys Val Asp Leu Ser Thr Leu Ser
            100                 105                 110

Phe Gly His Trp Gly Gln Gly Thr Gln Val Thr Val Ser Ile Thr
        115                 120                 125

<210> SEQ ID NO 34
<211> LENGTH: 125

```
<212> TYPE: PRT
<213> ORGANISM: artificial sequence
<220> FEATURE:
<223> OTHER INFORMATION: Polypeptide

<400> SEQUENCE: 34

Met Asp Val Gln Leu Gln Glu Ser Gly Gly Ser Val Gln Ala Gly
1               5                   10                  15

Gly Ser Leu Arg Leu Ser Cys Pro Ala Ser Gly Tyr Thr Phe Ser His
            20                  25                  30

Tyr Cys Met Gly Trp Leu Arg Gln Ala Pro Gly Lys Glu Arg Glu Glu
        35                  40                  45

Val Ala Thr Ile Asp Thr Asp Ser Thr Pro Thr Tyr Ala Asp Ser Val
    50                  55                  60

Met Gly Arg Phe Thr Ile Ser Arg Asp Asn Ala Asn Ala Leu Tyr
65                  70                  75                  80

Leu Gln Met Asn Asp Leu Lys Pro Glu Asp Thr Ser Met Tyr Tyr Cys
                85                  90                  95

Ala Thr Trp Met Gly Leu Arg Gly Ser Cys His Asp Arg Arg Leu Glu
            100                 105                 110

Val Arg Gly Gln Gly Thr Gln Val Thr Val Ser Ile Asn
        115                 120                 125

<210> SEQ ID NO 35
<211> LENGTH: 130
<212> TYPE: PRT
<213> ORGANISM: artificial sequence
<220> FEATURE:
<223> OTHER INFORMATION: Polypeptide

<400> SEQUENCE: 35

Met Asp Val Gln Leu Gln Glu Ser Gly Gly Ser Val Gln Ala Gly
1               5                   10                  15

Gly Ser Leu Arg Leu Ser Cys Ala Ala Ser Gly Tyr Thr Thr Ser Arg
            20                  25                  30

Leu Cys Met Ala Trp Phe Arg Gln Phe Pro Gly Lys Glu Arg Glu Gly
        35                  40                  45

Val Ala Asn Val Arg Leu Gly Gly Tyr Lys Pro Ala Tyr Ala Asp Ser
    50                  55                  60

Val Lys Gly Arg Phe Thr Leu Ser Glu Asp Ser Ala Lys Asn Thr Val
65                  70                  75                  80

Tyr Leu Glu Met Asn Ser Leu Gln Pro Glu Asp Thr Ala Met Tyr Tyr
                85                  90                  95

Cys Ala Ala Asp Pro Gly Gly Gly Ser Cys Pro Val Ala Leu Val
            100                 105                 110

Arg Gly Asp Phe Asp Tyr Trp Gly Gln Gly Thr Gln Val Thr Val Ser
        115                 120                 125

Ile Asn
    130

<210> SEQ ID NO 36
<211> LENGTH: 127
<212> TYPE: PRT
<213> ORGANISM: artificial sequence
<220> FEATURE:
<223> OTHER INFORMATION: Polypeptide

<400> SEQUENCE: 36

Met Asp Val Gln Leu Gln Glu Ser Gly Gly Gly Leu Val Gln Ala Gly
```

```
1               5                   10                  15
Gly Ser Leu Arg Leu Ser Cys Ala Val Ser Gly Tyr Pro Tyr Ser Ser
            20                  25                  30

Tyr Cys Met Gly Trp Phe Arg Gln Ala Pro Gly Lys Glu Arg Glu Gly
                35                  40                  45

Val Ala Ala Ile Asp Ser Asp Gly Arg Thr Arg Tyr Ala Asp Ser Val
        50                  55                  60

Lys Gly Arg Phe Thr Ile Ser Gln Asp Asn Ala Lys Asn Thr Leu Tyr
65                  70                  75                  80

Leu Gln Met Asn Arg Met Lys Pro Glu Asp Thr Ala Met Tyr Tyr Cys
                    85                  90                  95

Ala Ala Arg Phe Gly Pro Met Gly Cys Val Asp Leu Ser Thr Leu Ser
                100                 105                 110

Phe Gly His Trp Gly Gln Gly Thr Gln Val Thr Val Ser Ile Thr
            115                 120                 125
```

<210> SEQ ID NO 37
<211> LENGTH: 127
<212> TYPE: PRT
<213> ORGANISM: artificial sequence
<220> FEATURE:
<223> OTHER INFORMATION: Polypeptide

<400> SEQUENCE: 37

```
Met Asp Val Gln Leu Gln Glu Ser Gly Gly Gly Ser Val Gln Ala Gly
1               5                   10                  15

Gly Ser Leu Arg Leu Ser Cys Ala Ala Ser Gly Tyr Thr Tyr Ser Thr
            20                  25                  30

Tyr Cys Met Gly Trp Phe Arg Gln Ala Pro Gly Lys Glu Arg Glu Gly
                35                  40                  45

Val Ala Thr Ile Asp Ser Asp Gly Ser Thr Ser Tyr Ala Asp Ser Val
        50                  55                  60

Lys Gly Arg Phe Thr Ile Ser Arg Asp Asn Ala Lys Asn Thr Leu Asn
65                  70                  75                  80

Leu Gln Met Ser Ser Leu Lys Pro Glu Asp Thr Ala Met Tyr Tyr Cys
                    85                  90                  95

Ala Ala Arg Phe Gly Pro Met Gly Cys Val Asp Leu Ser Thr Leu Ser
                100                 105                 110

Phe Gly His Trp Gly Gln Gly Thr Gln Val Thr Val Ser Ile Thr
            115                 120                 125
```

<210> SEQ ID NO 38
<211> LENGTH: 378
<212> TYPE: DNA
<213> ORGANISM: artificial sequence
<220> FEATURE:
<223> OTHER INFORMATION: Polyribonucleotide

<400> SEQUENCE: 38

```
atggatgtgc agctgcagga gtctggagga ggctcggtgc aggctggagg gtctctgaga    60
ctctcctgtc agcctctgg atacacctta gtcactact gcatgggctg aaccgccag      120 gctccaggaa aggagcgcga ggaggtcgcg actattgata ctgatgatac ccaacctac    180 gcagactccg tgatgggccg attcaccatc tccagagata cgccaacaa cgctctgtat    240 ctgcaaatga cgacctgaa acctgaggac acttccatgt actactgtgc gatttggatg    300
aaattgcgag gtagctgcca cgataggcgt ctcgaagttc ggggccaggg cacccaggtc    360
```

```
accgtctcca tcaactag                                                  378
```

<210> SEQ ID NO 39
<211> LENGTH: 384
<212> TYPE: DNA
<213> ORGANISM: artificial sequence
<220> FEATURE:
<223> OTHER INFORMATION: Polyribonucleotide

<400> SEQUENCE: 39

```
atggatgtgc agctgcagga gtctggggga ggctcggtgc aggctggagg gtccctgaga    60
ctctcctgtg cagcctctgg atacacccac agtagttact gcatggcctg gttccgccag   120
gctccaggga gggagcgcga ggggtcgca  tctattgata gtgacggtac cacaagctac   180
gcagactccg tgaagggccg attcaccatc tcccaagaca acgccaagaa cacgctgtat   240
ctgcaaatga acagcctgaa acctgaggac actgccatgt actactgtgc ggcccgattt   300
gggcctatgg gttgtgtaga cctcagtacg ttgagctttg gcactgggg  ccaggggacc   360
caggtcaccg tctccatcac ttag                                          384
```

<210> SEQ ID NO 40
<211> LENGTH: 378
<212> TYPE: DNA
<213> ORGANISM: artificial sequence
<220> FEATURE:
<223> OTHER INFORMATION: Polyribonucleotide

<400> SEQUENCE: 40

```
atggatgtgc agctgcagga gtctggagga ggctcggtgc aggctggagg gtctctgaga    60
ctctcctgtc cagcctctgg atacaccttc agtcactact gcatgggttg gctccgccag   120
gctccaggaa aggagcgcga ggaggtcgcg actattgata ctgatagtac cccaacctac   180
gcagactccg tgatgggccg attcaccatc tccagagata acgccaacaa cgctctgtat   240
ctgcaaatga acgacctgaa acctgaggac acttccatgt actactgtgc gacttggatg   300
ggattgcgag gtagctgcca cgacaggcgt ctcgaagttc ggggcaggg  cacccaggtc   360
accgtctcca tcaactag                                                 378
```

<210> SEQ ID NO 41
<211> LENGTH: 393
<212> TYPE: DNA
<213> ORGANISM: artificial sequence
<220> FEATURE:
<223> OTHER INFORMATION: Polyribonucleotide

<400> SEQUENCE: 41

```
atggatgtgc agctgcagga gtctggagga gggtcggtgc aggctggagg gtctctgaga    60
ctctcctgtg cagcctctgg atacaccacc agtcgccttt gcatggcctg gttccgccag   120
tttccaggga aggagcgcga ggggtcgcg  aatgttaggc ttggtggtta taagccagcc   180
tatgccgact ccgtgaaggg ccgattcacc ctctccgaag acagcgccaa gaacacggtg   240
tatctcgaaa tgaacagcct ccaacctgag gacactgcca tgtattactg tgcggcagat   300
cccgggggcg gtggtagctg tccggtcgcc ctagttcgag gtgactttga ttactggggc   360
caggggaccc aggtcaccgt ctccatcaac tag                                393
```

<210> SEQ ID NO 42
<211> LENGTH: 384
<212> TYPE: DNA
<213> ORGANISM: artificial sequence

```
<220> FEATURE:
<223> OTHER INFORMATION: Polyribonucleotide

<400> SEQUENCE: 42
atggatgtgc agctgcagga gtctggagga ggcttggtgc aggctggagg gtctctgaga      60
ctctcctgtg cagtctctgg atacccctac agtagctact gcatgggctg gttccgccag     120
gctccaggga aggagcgcga gggggtcgct gctattgata gtgatggtag gacaaggtac     180
gcagactccg tgaagggccg attcaccatc tcccaagaca cgccaagaa  cactctgtat     240 ctgcaaatga acagaatgaa acctgaggac actgccatgt actactgtgc ggcccgattt     300
gggcctatgg gttgtgtaga cctcagtacg ttgagctttg ggcactgggg ccaggggacc     360
caggtcaccg tctccatcac ttag                                            384

<210> SEQ ID NO 43
<211> LENGTH: 456
<212> TYPE: DNA
<213> ORGANISM: artificial sequence
<220> FEATURE:
<223> OTHER INFORMATION: Polyribonucleotide

<400> SEQUENCE: 43
atggatgtgc agctgcagga gtctggagga ggctcggtgc aggctggagg gtctctgaga      60
ctctcctgtg cagcctctgg atacacctac agtacgtact gcatgggctg gttccgccag     120
gctccaggaa aggagcgcga gggggtcgca actattgata gtgatggtag cacaagctac     180
gcagactccg tgaagggccg attcaccatc tccagagaca cgccaagaa  cactctgaat     240 ctacaaatga gcagcctgaa acctgaggac actgccatgt actactgtgc ggcccgattt     300
gggcctatgg gttgtgtaga cctcagtacg ttgagctttg ggcactgggg ccaggggacc     360
caggtcaccg tctccatcac tagtggccag gccggccagc accatcacca tcaccatggc     420
gcatacccgt acgacgttcc ggactacgct tcttag                               456

<210> SEQ ID NO 44
<211> LENGTH: 1170
<212> TYPE: DNA
<213> ORGANISM: Pseudomonas

<400> SEQUENCE: 44
ggatccggcg gtggtggtag tggtggtggt ggcagtggtg gtggtggtag cggtggtggc      60
ggtagtgccg cagcactgga aggcggtagt ctggcagccc tgaccgcaca tcaggcatgt     120
catctgcctc tggaaacctt cacccgccac cgtcaaccgc gtggttggga acagctggaa     180
caatgtggct atccggtgca gcgcctggtt gcactgtatc tggccgcccg cctgagctgg     240
aatcaggtgg atcaggttat tcgcaacgca ctggcaagcc cggtagcgg  tggtgatctg     300 ggcgaagcca ttcgcgagca gccggaacag gcacgtctgg ccctgaccct ggcagcagca     360
gaaagcgaac gttttgttcg ccagggtacc ggcaacgatg aggcaggtgc agccaatgcc     420
gatgttgtga gtctgacctg tccggttgcc gcaggtgaat gtgcaggccc ggcagatagt     480
ggcgacgcac tgctggaacg taactacccg accggtgccg aatttctggg tgacggcggt     540
gacgtgagct tcagcacacg tggcacacag aattggacag tggagcgtct gctgcaggcc     600
catcgtcagc tggaagaacg cggctatgtt ttcgtgggct accatggcac attcctggaa     660
gccgcccaga gcatcgtttt tggtggtgtt cgtgcccgca gccaggatct ggacgcaatt     720
tggcgcggct tttatattgc aggcgatccg gccttagcct atggctatgc acaggatcag     780
```

```
gaaccggatg cccgcggtcg cattcgtaac ggcgccttac tgcgcgtgta tgtgccgcgt    840
agtagcctgc cgggctttta tcgtaccagc ctgacactgg ccgcccctga agcagccggt    900
gaagtggaac gtctgattgg ccatccgctg ccgttacgcc tggatgccat taccggtccg    960
gaagaagagg gcggccgtct ggaaaccatt ctgggctggc cgctggcaga acgtacagtg   1020
gtgattccga gcgccatccc taccgatccg cgcaatgtgg gtggtgacct agacccgagc   1080
agtatcccgg acaaagagca ggcaattagc gccctgccgg attatgccag ccaaccgggc   1140
aaaccgccga agatgaact gtaactcgag                                     1170
```

<210> SEQ ID NO 45
<211> LENGTH: 22
<212> TYPE: DNA
<213> ORGANISM: artificial sequence
<220> FEATURE:
<223> OTHER INFORMATION: Polyribonucleotide

<400> SEQUENCE: 45
gtcctggctc tcttctacaa gg                                              22

<210> SEQ ID NO 46
<211> LENGTH: 22
<212> TYPE: DNA
<213> ORGANISM: artificial sequence
<220> FEATURE:
<223> OTHER INFORMATION: Polyribonucleotide

<400> SEQUENCE: 46
ggtacgtgct gttgaactgt tc                                              22

<210> SEQ ID NO 47
<211> LENGTH: 39
<212> TYPE: DNA
<213> ORGANISM: artificial sequence
<220> FEATURE:
<223> OTHER INFORMATION: Polyribonucleotide

<400> SEQUENCE: 47
cgagctcatg gatgtgcagc tgcaggagtc tggaggagg                            39

<210> SEQ ID NO 48
<211> LENGTH: 29
<212> TYPE: DNA
<213> ORGANISM: artificial sequence
<220> FEATURE:
<223> OTHER INFORMATION: Polyribonucleotide

<400> SEQUENCE: 48
ggactagtga tggagacggt gacctgggt                                       29

<210> SEQ ID NO 49
<211> LENGTH: 4
<212> TYPE: PRT
<213> ORGANISM: artificial sequence
<220> FEATURE:
<223> OTHER INFORMATION: Endoplasmic reticulum retention sequence

<400> SEQUENCE: 49

Lys Asp Glu Leu
1

<210> SEQ ID NO 50
<211> LENGTH: 5
<212> TYPE: PRT

```
<213> ORGANISM: artificial sequence
<220> FEATURE:
<223> OTHER INFORMATION: linker

<400> SEQUENCE: 50

Gly Gly Gly Gly Ser
1               5

<210> SEQ ID NO 51
<211> LENGTH: 5
<212> TYPE: PRT
<213> ORGANISM: artificial sequence
<220> FEATURE:
<223> OTHER INFORMATION: Polypeptide

<400> SEQUENCE: 51

Arg Glu Asp Leu Lys
1               5
```

CD7 NANOBODIES, ENCODING SEQUENCE AND USE THEREOF

TECHNICAL FIELD

The present invention belongs to the biomedical or biopharmaceutical technical field, and relates to a nanobody against human CD7 molecule, encoding sequence and use thereof.

BACKGROUND ART

In 1993, Hamers-Casterman and his colleagues discovered a specific type of antibody in camelids, i.e. heavy chain antibodies (HCAbs) that naturally lack light chains. A single domain antibody (sdAb) consisting of only one heavy chain variable region is obtained by cloning its variable region. Its crystal structure is elliptical, 2.5 nm in diameter and 4 nm in height. So it is also called Nanobody (Nb; 15 kDa) which is the smallest functional antigen-binding fragment at this stage. Nanobodies have many unique properties compared with conventional antibodies: 1) Nanobodies are highly homologous to the human VH family 3 and 4 and therefore have little immunogenicity; 2) Nanobodies have a small molecular weight of only about 15 kDa and a simple structure which facilitate them to be expressed in microorganisms in a large scale and easy to be purified; 3) Nanobodies can recognize a large number of epitopes, including epitopes hidden in the molecular cleft; 4) Nanobodies can easily penetrate the tissue due to the small molecular weight to reach the site which is difficult to be reached by conventional antibodies; 5) Nanobodies are highly soluble and stable at denaturing or high temperature environments.

Human CD7 molecule is a cell surface glycoprotein having a molecular weight of about 40 kDa and belongs to the immunoglobulin superfamily. CD7 molecules are mainly expressed on the surfaces of most of the thymocytes, 85% of the peripheral blood T lymphocytes and natural killer cells. Although current studies have shown that the specific function of CD7 molecules is not yet clear, but experiments show that the T lymphocytes of CD7-deficient mice react normally to stimulation and the cell growth and proliferation are not effected when the antibody binding CD7 molecules on human T lymphocytes. At the same time, an important property of the CD7 molecule is that when it binds to its antibody, it starts endocytosis immediately. On the basis of this important property, several studies have been made by conjugating immunotoxins to CD7 molecules for target delivery to human leukemia and lymphoma cells thereby achieving the purpose of treating diseases and coupling immunotoxins to treat acute graft-versus-host diseases. These experiments have been carried out in clinical trials. At the same time, it has been studied to treat HIV infection by conjugating protein to CD7 molecules for targeted delivery siRNAs to T lymphocytes. However, these experiments were performed on single-chain antibodies (scFv; 30 kDa) isolated from conventional antibodies. Single-chain antibodies are difficult to invade into tissues and cells due to their relatively large molecular weight while nanobodies have small molecular weight. Meanwhile, single-chain antibodies are difficult to be expressed in prokaryotic expression system in a soluble form. Nanobodies are easy to be expressed in prokaryotic expression system in a soluble form and easy to be renatured. Therefore, preparing human CD7 nanobodies for disease treatment may be one of the alternatives with more effective and lower cost.

At present, there is no research report on the specific nanobodies directed against human CD7 epitopes.

SUMMARY OF INVENTION

Object of the invention: One object of the present invention is to provide a nanobody directed against a human CD7 molecule while providing the coding sequence of the nanobody and the use of the nanobody for preparing detection reagents or kits.

Technical solutions: In order to achieve the above object, in the first aspect of the present invention, a VHH chain of a human CD7 nanobody is provided, comprising framework regions (FRs) and complementarity determining regions (CDRs), wherein the framework regions (FRs) are selected from the following amino acid sequences FR1 to FR4:

FR1 as shown in SEQ ID NO: 1, FR2 as shown in SEQ ID NO: 2, FR3 as shown in SEQ ID NO: 3, FR4 as shown in SEQ ID NO: 4;

or FR1 as shown in SEQ ID NO: 5, FR2 as shown in SEQ ID NO: 6, FR3 as shown in SEQ ID NO: 7, FR4 as shown in SEQ ID NO: 8;

or FR1 as shown in SEQ ID NO: 1, FR2 as shown in SEQ ID NO: 9, FR3 as shown in SEQ ID NO: 3, FR4 as shown in SEQ ID NO: 4;

or FR1 as shown in SEQ ID NO: 5, FR2 as shown in SEQ ID NO: 10, FR3 as shown in SEQ ID NO: 11, FR4 as shown in SEQ ID NO: 12;

or FR1 as shown in SEQ ID NO: 13, FR2 as shown in SEQ ID NO: 14, FR3 as shown in SEQ ID NO: 15, FR4 as shown in SEQ ID NO: 8;

or FR1 as shown in SEQ ID NO: 5, FR2 as shown in SEQ ID NO: 14, FR3 as shown in SEQ ID NO: 16, FR4 as shown in SEQ ID NO: 8;

the complementarity determining regions (CDRs) selected from the following amino acid sequences CDR1 to CDR3:

CDR1 as shown in SEQ ID NO: 17, CDR2 as shown in SEQ ID NO: 18, CDR3 as shown in SEQ ID NO: 19;

or CDR1 as shown in SEQ ID NO: 20, CDR2 as shown in SEQ ID NO: 21, CDR3 as shown in SEQ ID NO: 22;

or CDR1 as shown in SEQ ID NO: 17, CDR2 as shown in SEQ ID NO: 23, CDR3 as shown in SEQ ID NO: 24;

or CDR1 as shown in SEQ ID NO: 25, CDR2 as shown in SEQ ID NO: 26, CDR3 as shown in SEQ ID NO: 27;

or CDR1 as shown in SEQ ID NO: 28, CDR2 as shown in SEQ ID NO: 29, CDR3 as shown in SEQ ID NO: 22;

or CDR1 as shown in SEQ ID NO: 30, CDR2 as shown in SEQ ID NO: 31, CDR3 as shown in SEQ ID NO: 22.

Preferably, it has the amino acid sequence as shown in SEQ ID NO: 32, SEQ ID NO: 33, SEQ ID NO: 34, SEQ ID NO: 35, SEQ ID NO: 36, or SEQ ID NO: 37.

In the second aspect of the present invention, it provides a human CD7 nanobody wherein the nanobody is directed against a human CD7 molecule epitope and comprises a VHH chain having the amino acid sequence of SEQ ID NO: 32, SEQ ID NO: 33, SEQ ID NO: 34, SEQ ID NO: 35, SEQ ID NO: 36, or SEQ ID NO: 37.

In the third aspect of the present invention, it provides a DNA molecule encoding a protein selected from the group consisting of the VHH chain of the human CD7 nanobody of claim 1 or 2 and the human CD7 nanobody of claim 3.

Preferably, the DNA molecule has a DNA sequence selected from the group consisting of SEQ ID NO: 38, SEQ ID NO: 39, SEQ ID NO: 40, SEQ ID NO: 41, SEQ ID NO: 42 and SEQ ID NO: 43.

In the fourth aspect of the present invention, it provides a vector comprising a nucleic acid sequence as shown in SEQ ID NO: 38, SEQ ID NO: 39, SEQ ID NO: 40, SEQ ID NO: 41, SEQ ID NO: 42 or SEQ ID NO: 43.

In the fifth aspect of the invention, it provides a host cell expressing a nanobody against human CD7.

In the sixth aspect of the invention, it provides a use of the human CD7 nanobody of the present invention for detecting a human CD7 molecule.

In the seventh aspect of the invention, it provides the use of the human CD7 nanobody of the present invention for flow cytometry and cellular immunofluorescence assays.

In another preferred embodiment, the use is for non-diagnostic purposes.

In the eighth aspect of the invention, it provides a heavy chain variable region of an anti-human CD7 antibody, wherein the heavy chain variable region comprises three complementarity determining regions CDR1, CDR2, and CDR3, wherein CDR1 is selected from the group consisting of SEQ ID NOS: 17, 20, 25, 28, and 30;

CDR2 is selected from the group consisting of SEQ ID NO: 18, 21, 23, 26, 29, and 31;

CDR3 is selected from the group consisting of SEQ ID NO: 19, 22, 24, and 27.

In another preferred embodiment, the heavy chain variable region comprises:

CDR1 as shown in SEQ ID NO: 17, CDR2 as shown in SEQ ID NO: 18, CDR3 as shown in SEQ ID NO: 19;

or CDR1 as shown in SEQ ID NO: 20, CDR2 as shown in SEQ ID NO: 21, CDR3 as shown in SEQ ID NO: 22;

or CDR1 as shown in SEQ ID NO: 17, CDR2 as shown in SEQ ID NO: 23, CDR3 as shown in SEQ ID NO: 24;

or CDR1 as shown in SEQ ID NO: 25, CDR2 as shown in SEQ ID NO: 26, CDR3 as shown in SEQ ID NO: 27;

or CDR1 as shown in SEQ ID NO: 28, CDR2 as shown in SEQ ID NO: 29, CDR3 as shown in SEQ ID NO: 22;

or CDR1 as shown in SEQ ID NO: 30, CDR2 as shown in SEQ ID NO: 31, CDR3 as shown in SEQ ID NO: 22.

Preferably, it has the amino acid sequence as shown in SEQ ID NO: 32, SEQ ID NO: 33, SEQ ID NO: 34, SEQ ID NO: 35, SEQ ID NO: 36, or SEQ ID NO: 37.

In the ninth aspect of the invention, it provides an antibody comprising a heavy chain variable region according to the eighth aspect of the present invention.

In another preferred embodiment, the antibody comprises a VHH chain having the amino acid sequence of SEQ ID NO: 32, SEQ ID NO: 33, SEQ ID NO: 34, SEQ ID NO: 35, SEQ ID NO: 36, or SEQ ID NO: 37.

In another preferred embodiment, the antibody is specific against CD7 protein.

In another preferred embodiment, the antibody is a nanobody.

In the tenth aspect of the invention, it provides a recombinant protein comprising:

(i) a sequence of the heavy chain variable region according to the eighth aspect of the present invention or a sequence of the antibody according to the ninth aspect of the present invention; and (ii) optionally a tag sequence that facilitates expression and/or purification.

In another preferred embodiment, the tag sequence comprises a 6His tag and an HA tag.

In another preferred embodiment, the recombinant protein specifically binds to a CD7 protein.

In the eleventh aspect of the present invention, it provides an immunoconjugate comprising:

(a) a VHH chain of the human CD7 nanobody according to the first aspect of the present invention, the human CD7 nanobody according to the second aspect of the present invention, the heavy chain variable region according to the eighth aspect of the present invention, an antibody according to the ninth aspect of the present invention, or a recombinant protein according to the tenth aspect of the present invention; and (b) a coupling moiety selected from the group consisting of a detectable label, a drug, a toxin, a cytokine, a radionuclide, or an enzyme.

In another preferred embodiment, the coupling moiety is selected from the group consisting of a fluorescent or luminescent label, a radiolabel, a MRI (magnetic resonance imaging) or CT (computed X-ray tomography) contrast agent, or an enzyme capable of producing detectable products, a radionuclide, a biotoxin, a cytokine (e.g., IL-2, etc.), an antibody, an antibody Fc fragment, a scFv antibody fragment, a gold nanoparticle/nanorod, a virus particle, a liposome, a nano-magnetic particle, a prodrug activating enzyme (e.g., DT-diaphorase (DTD) or a biphenyl hydrolase-like protein (BPHL)), a chemotherapeutic agent (e.g., cisplatin) or a nano-particle in any form.

In another preferred embodiment, the coupling moiety is Pseudomonas exotoxin or a fragment thereof.

In another preferred embodiment, the immunoconjugate comprises a multivalent (e.g., bivalent) VHH chain of the human CD7 nanobody according to the first aspect of the present invention, human CD7 nanobody according to the second aspect of the present invention, heavy chain variable region according to the eighth aspect of the present invention, antibody according to the ninth aspect of the present invention, or recombinant protein according to the tenth aspect of the present invention. The term "multivalent" refers to the amino acid sequence of the immunoconjugate comprising a plurality of repeating sequences of the VHH chain of the human CD7 nanobody according to the first aspect of the present invention, the human CD7 nanobody according to the second aspect of the present invention, the heavy chain variable region according to the eighth aspect of the present invention, an antibody according to the ninth aspect of the present invention, or a recombinant protein according to the tenth aspect of the present invention.

In the twelfth aspect of the present invention, it provides a pharmaceutical composition comprising:

(i) the heavy chain variable region according to the eighth aspect of the present invention, an antibody according to the ninth aspect of the present invention, or a recombinant protein according to the tenth aspect of the present invention, or the immunoconjugate according to the eleventh aspect of the present invention; and (ii) a pharmaceutically acceptable carrier.

In another preferred embodiment, the pharmaceutical composition is in the form of an injection.

In another preferred embodiment, the pharmaceutical composition is used for preparing a medicament for treating a tumor selected from the group consisting of gastric cancer, liver cancer, leukemia, kidney cancer, lung cancer, small bowel cancer, bone cancer, prostate cancer, colorectal cancer, breast cancer, colon cancer, prostate cancer, cervical cancer, lymphoma, adrenal tumor, or bladder tumor.

In the thirteenth aspect of the present invention, it provides a use of a heavy chain variable region according to the first aspect of the present invention, a heavy chain according to the second aspect of the present invention, an antibody according to the fifth aspect of the present invention, or a recombinant protein according to the sixth aspect of the present invention, or the immunoconjugate according to the tenth aspect of the present invention for preparing an agent, a reagent, a detection plate or a kit;

wherein the reagent, the detection plate or the kit is used for detecting a CD7 protein in a sample;

the agent is used for the treatment or prevention of tumors expressing CD7 proteins.

In another preferred example, the tumor includes gastric cancer, lymphoma, liver cancer, leukemia, kidney cancer, lung cancer, small intestine cancer, bone cancer, prostate cancer, colorectal cancer, breast cancer, colon cancer, prostate cancer, or adrenal tumor.

In the fourteenth aspect of the present invention, it provides a method of detecting a CD7 protein in a sample, wherein the method comprises the steps of:
(1) contacting a sample with the antibody according to the fifth aspect of the invention;
(2) detecting whether an antigen-antibody complex is formed, wherein the formation of the complex indicates the presence of a CD7 protein in the sample.

In the fifteenth aspect of the invention, it provides a method for preparing a recombinant polypeptide, which comprises:
(a) culturing the host cell according to the ninth aspect of the invention under conditions suitable for expression;
(b) isolating the recombinant polypeptide from the culture, wherein the recombinant polypeptide is the antibody according to the fifth aspect of the present invention or the recombinant protein according to the sixth aspect of the present invention.

In the sixteenth aspect of the present invention, it provides a method of treating a disease comprising administering a nanobody or immunoconjugate of the invention to a subject in need thereof.

Advantageous Effects (1) According to the present invention, a cancer cell line highly expressing human CD7 molecule was selected by flow detection method and the cell line was treated to be immunogenic. And then a camel was immunized with the cell line. The lymphocytes from the peripheral blood of the camel were extracted to prepare nanobody Immune Gene Bank. Finally, the CD7 nanobody was screened on a human renal epithelial cell line (293T cell line) to obtain a human CD7-specific nanobody gene. This gene was cloned into the prokaryotic expression vector and transformed into E. coli. The nanobody strain, which could be efficiently expressed in E. coli, was therefore established;

(2) The present invention utilizes the cells highly expressing target antigens to immunize the camel, and the obtained immunological library is abundant. In addition to screening the antibody against the target antigen, antibodies against other highly expressed molecules on the immune cells can also be screened. Compared with using a polypeptide or a protein as a antigen to perform immunization which can only produce one type of antibody against the selected antigen the present invention can save cost, time and manpower;

(3) The present invention uses cells to perform the screening of anti-human CD7 molecule nanobodies from a prepared nanobody library to obtain molecules specifically recognizing human CD7 with natural activity, and this specific nanobody can be used for flow cytometry and cellular immunofluorescence assays.

DESCRIPTION OF FIGURES

FIG. 5A is a chart for showing OD450 values of 32 randomly selected phage clones with 293T cells. FIG. 5B is a chart for showing OD450 values of 32 randomly selected phage clones with 293T-CD7 cells. x-axis of FIGS. 5A and 5B represents 32 random selected phage clones, and y-axis of FIGS. 5A and 5B represents the OD450 values obtained from the ELISA for the 32 phage clones.

FIG. 6A shows the SDS-PAGE of purified nanobodies of VHH6 clones. Lane 1 of FIG. 6A shows protein marker, and Lane 2 of FIG. 6A shows purified nanobodies of VHH6 clones. FIG. 6B shows SDS-PAGE of purified nanobodies of VHH10 clones. Lane 1 of FIG. 6B shows protein marker, and the other lanes of FIG. 6B shows purified nanobodies of VHH10 clones.

FIG. 10A shows flow cytometry assay of the CD7 negative cell line H460 transfected with pcDNA3.1-hCD7. FIG. 10B shows flow cytometry assay of the CD7 negative cell line H460 transfected with pcDNA3.1. x-axis of FIGS. 10A and 10B represents the CD7 expression on H460 cells detected in different experimental groups, and y-axis of FIGS. 10A and 10B represents the cell particle size.

FIG. 12A shows confocal fluorescence microscopy image of Jurkat cells (CD7 positive) stained with DAPI and Alexa Fluor 488, and FIG. 12B shows confocal fluorescence microscopy image of RPMI8226 cells (CD7 negative) stained with DAPI and Alexa Fluor 488. VHH6 nanobodies were tested.

FIG. 13A schematically illustrates the PG001 construct. 6×His is a six histidine tag; VHH-6 is a CD7-specific nanobody; 4 ($G_4S$) linker is a linker consisting of four GGGGS (SEQ ID NO: 50); ETA is composed of Pseudomonas exotoxin Domain II and Domain III; and KDEL (SEQ ID NO: 49) is an Endoplasmic reticulum retention sequence. The molecular weights are estimated based on their amino acid sequences. FIG. 13B shows a Coomassie brilliant blue stained SDS-PAGE of recombinant immunotoxin PG001 purified by nickel column affinity chromatography. Lane 1 is protein marker, and the other lanes shows purified PG001. FIG. 13C shows immunoblot analysis of recombinant immunotoxin PG001. Lanes 1 and 2 in FIG. 13C show immunoblot results of PG001.

FIG. 15A shows inhibition rates of cell growth of CD7-positive Jurkat cells (black grid) and CD7-negative RPMI8226 cells (white grid) after treated with a concentration gradient of the obtained high-purity PG001 for 72 hours. FIG. 15B shows inhibition rates of cell growth of CD7-positive CEM cells (black grid) and CD7-negative H460 cells (white grid) after treated with a concentration gradient of the obtained high-purity PG001 for 72 hours. Cell growth inhibition was measured by WST-8. Mean values were obtained from three independent experiments (Jurkat, CEM, RPMI8226, H460). Standard deviations are represented by error bar.

FIG. 19A schematically illustrate a PG002 construct. VHH-6 is a CD7-specific nanobody; 4($G_4S$) linker is a linker consisting of four GGGGS (SEQ ID NO: 50); ETA is composed of Pseudomonas exotoxin Domain II and Domain III; and KDEL (SEQ ID NO: 49) is an Endoplasmic reticulum retention sequence. FIG. 19B shows Coomassie brilliant blue stained SDS-PAGE of an affinity purified nanobody Immunotoxin PG002. Lane 1 is protein marker, and the other lanes shows purified PG002. Lane 1 of FIG. 19B shows protein marker, and the other lanes of FIG. 19B show purified PG002. FIG. 19C schematically shows cell growth inhibition effects of the purified PG002 on CD7-positive Jurkat cells (black grid), CD7-positive CEM cells (gray grid), and CD7-negative RPMI8226 cells (white grid). The cells were respectively treated with a centration gradient of the purified PG002 for 72 hours. Cell growth inhibitions were detected by WST-8 kit. Mean values were obtained from three independent experiments (Jurkat, CEM, RPMI8226). Standard deviations were represented by error bars.

DETAILED DESCRIPTION OF INVENTION

Figure 1:
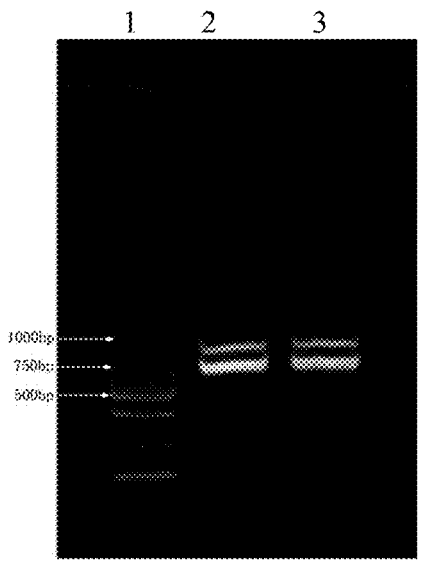
FIG. 1 shows an agarose gel electrophoresis of the first round PCR products. Fragments of 650~750 bp are excised from the gel and recovered. Lane 1 is DNA marker, the large fragments (about 1000 bp) visible at Lane 2 and Lane 3 represent the antibody fragments of conventional camelid antibodies, and the small fragments (about 750 bp) visible at Lane 2 and Lane 3 represent fragments of heavy chain antibodies.

The invention will now be described in further detail with reference to the accompanying drawings. The following examples are only intended to more clearly illustrate the technical solution of the present invention and are not intended to limit the scope of the invention.

Through extensive and intensive researches and a large number of screenings, the inventors successfully obtained a class of anti-CD7 nanobodies. The experimental results showed that the nanobody is not only highly specific but also can significantly efficient bind with CD7 molecules of the CD7 molecule-expressing cell lines and T lymphocyte Cells or natural killer cells. This type of antibodies can be modified to deliver functional molecules (toxins or small molecules of RNA) to CD7 positive cells for killing or for other functional studies. Based on this discovery, the inventors have completed the present invention.

In the present invention, a Xinjiang Bactrian camel was first immunized with a CD7 high expressive cell line Jurkat cells ($5\times10^6$). After 7 times of consecutive immunizations, the peripheral blood lymphocytes of the Bactrian camel were extracted from the Bactrian camel and a single domain heavy chain antibody library was successfully constructed. CD7-specific nanobodies were then screened on 293T-CD7⁻ (the original 293T cells do not express CD7) and 293T-CD7⁺ (stable transfected 293T-CD7 cell lines) cell lines, resulting in a Nanobody strain highly efficient expressed in E. coli.

The term "antibody" or "immunoglobulin" as used herein refers to a heterotetrameric glycoprotein having the same structural feature of about 150,000 Daltons consisting of two identical light chains (L) and two identical heavy chains (H). Each light chain is linked to a heavy chain by a covalent disulfide bond, and the numbers of disulfide bonds between the heavy chains of different immunoglobulin isoforms are different. Each heavy and light chain also has regularly spaced intrachain disulfide bonds. One end of each heavy chain has a variable region (VH) followed by a plurality of constant regions. There is a variable region (VL) at one end of each chain and a constant region at the other end; the constant region of the light chain corresponds to the first constant region of the heavy chain; the variable region of the light chain corresponds to the variable region of the heavy chain. There is an interface formed between the variable regions of the light and heavy chains by particular amino acid residues.

As used herein, the terms "single domain antibody (VHH)" and "nanobody" have the same meaning, referring to a single domain antibody (VHH) consisting of only one heavy chain variable region constructed by cloning the variable region of an antibody heavy chain, and it is the smallest antigen-binding fragment with complete function. Generally, a single domain antibody (VHH) consisting of only one heavy chain variable region is constructed by cloning the variable region of the heavy chain of the antibody after obtaining an antibody naturally lacking a light chain and a heavy chain constant region 1 (CH1).

As used herein, the term "variable" means that some certain portions of the variable region of an antibody differ in sequence and contribute to the binding and specificity of each particular antibody to its particular antigen. However, the variability is not evenly distributed throughout the antibody variable region. It is concentrated in three regions in the light and heavy chain variable regions called complementarity determining regions (CDRs) or hypervariable regions. The more conserved portions of the variable regions are referred as framework regions (FRs). The variable regions of the natural heavy and light chains each comprises four FR regions, which are in a substantially β-folded configuration, and are linked by three CDRs that form the linker ring and, in some cases, form a partial β-folded structure. The CDRs in each chain stand close together through FR regions and form the antigen-binding site of the antibody together with the CDRs of the other chain (see Kabat et al., NIH Publ. No. 91-3242, Vol. I, 647-669 (1991)). Constant regions are not directly involved in the binding of the antibodies to the antigens, but they exhibit different effector functions, such as antibody-dependent cellular cytotoxicity involved in antibodies.

As known to those skilled in the art, the immunoconjugates and fusion expression products include conjugates formed by drugs, toxins, cytokines, radionuclides, enzymes and other diagnostic or therapeutic molecules binding to the antibodies or the fragments thereof of the invention. The present invention also includes cell surface markers or antigens that bind to the anti-CD7 protein antibodies or the fragments thereof.

As used herein, the terms "heavy chain variable region" and "VH" are used interchangeably.

As used herein, the terms "variable region" and "complementarity determining region (CDR)" are used interchangeably.

In a preferred embodiment of the invention, the heavy chain variable region of the antibody comprises three complementarity determining regions CDR1, CDR2, and CDR3, wherein CDR1 is selected from the group consisting of SEQ ID NOs: 17, 20, 25, 28, and 30;

CDR2 is selected from the group consisting of SEQ ID NOs: 18, 21, 23, 26, 29, and 31;

CDR3 is selected from the group consisting of SEQ ID NOs: 19, 22, 24, and 27.

In another preferred embodiment, the heavy chain variable region has an amino acid sequence of SEQ ID NO: 32, SEQ ID NO: 33, SEQ ID NO: 34, SEQ ID NO: 35, SEQ ID NO: 36 or SEQ ID NO: 37.

In a preferred embodiment of the invention, the heavy chain of said antibody comprises said heavy chain variable region and a heavy chain constant region.

In the present invention, the terms "antibody of the present invention", "protein of the present invention" or "polypeptide of the present invention" are used interchangeably and all refer to polypeptides that specifically bind to CD7 protein, for example, a protein or polypeptide comprising a heavy chain variable region (such as any amino acid sequence of SEQ ID NO: 32-37). They may or may not contain a starting methionine.

The present invention also provides other proteins or fusion expression products having the antibodies of the invention. In particular, the present invention includes any protein or protein conjugate and a fusion expression product (i.e., an immunoconjugate and a fusion expression product) comprising a heavy chain containing a variable region as long as the variable region is identical, or at least 90% homologous, preferably at least 95% homologous, with the heavy chain variable region of the antibody of the invention.

In general, the antigen-binding properties of an antibody can be described by three specific regions located in the heavy chain variable region, referring as variable regions (CDRs), and separated into four framework regions (FRs). The sequences of four FRs amino acids are relatively conservative and do not directly participate in the binding reaction. A cyclic structure are formed by these CDRs which are close to each other in the spatial structure by the β-folds formed by the FRs between them, and the CDRs on the heavy chains and the CDRs on the corresponding light chains constitute the antigen-binding sites of the antibody.

The amino acid sequence of the same type of antibody can be used to determine which amino acids have constituted the FR or CDR region.

The variable regions of the heavy chains of the antibodies of the invention are of particular interest because at least parts of them are involved in binding to an antigen. Thus, the invention encompasses those molecules having an antibody heavy chain variable region with CDRs as long as their CDRs have a homology of more than 90% (preferably more than 95%, optimally more than 98%) to the CDRs identified herein.

The invention includes not only intact antibodies but also fragments of antibodies with immunological activity or fusion proteins formed by antibodies with other sequences. Accordingly, the invention also includes active fragments, derivatives, and analogs of said antibodies.

As used herein, the terms "fragments", "derivatives" and "analogs" refer to the polypeptides that substantially maintain the same biological function or activity of the antibodies of the invention. The polypeptide fragments, derivatives or analogs of the present invention may be (i) a polypeptide with one or more conservative or non-conservative amino acid residues (preferably the conservative amino acid residues) being substituted, while such a substituted amino acid residue may or may not be encoded by a genetic code, or (ii) a polypeptide having substituted group(s) in one or more amino acid residues, or (iii) a polypeptide formed by fusion of the mature polypeptide with another compound (such as the compound that prolongs the half-life of the polypeptide, such as polyethylene glycol), or (iv) a polypeptide with additional amino acid sequence fused to said polypeptide sequence, such as fusion proteins formed by fusion with leader sequence, secretion sequence or sequence used to purify the polypeptide, or a fusion protein formed with a 6His tag. According to the teachings of the present application, these fragments, derivatives, and analogs are within the scope commonly known by the skilled person.

An antibody of the present invention refers to a polypeptide comprising the CDRs regions having CD7 protein binding activity. The term also includes a variant form of the polypeptide comprising the above CDRs regions having the same function as the antibodies of the invention. These variations include, but are not limited to, deletion, insert and/or replacement of one or more amino acids (typically 1-50, preferably 1-30, more preferably 1-20, most preferably 1-10), and adding one or more (typically 20 or less, preferably 10 or less, more preferably 5 or less) amino acids at the C-terminus and/or N-terminus. For example, in the art, replacement with similar or similar amino acids does not normally alter the function of the protein. Also, for example, the addition of one or several amino acids at the C-terminus and/or the N-terminus will not normally alter the function of the protein. The term also includes the active fragments and active derivatives of the antibodies of the invention.

The mutated forms of the polypeptide include homologous sequences, conserved variants, allelic variants, natural mutants, induced mutants, proteins encoded by DNA that hybridizes to the encoded DNA of the antibodies of the invention under high or low stringency conditions, and polypeptides or proteins obtained using antisera against antibodies of the invention.

The present invention also provides other polypeptides, such as fusion proteins comprising a human antibody or a fragment thereof. In addition to the substantially full length polypeptides, the present invention also encompasses fragments of antibodies of the invention. Typically, the fragment has at least about 50 consecutive amino acids of the antibody of the invention, preferably at least about 50 consecutive amino acids, more preferably at least about 80 consecutive amino acids, and most preferably at least about 100 consecutive amino acids.

In the present invention, the "conserved variants of the antibodies of the present invention" refers to the polypeptides formed by replacing at most 10, preferably at most 8, more preferably at most 5, and most preferably 3 amino acid of the amino acid sequence of the polypeptide of the present invention with the amino acid having similar or analogous property. These conservative variant polypeptides are preferably formed by carrying out the amino acid replacement according to Table I.

TABLE I

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides a polynucleotide molecule encoding the above antibody or fragment thereof or a fusion protein thereof. The polynucleotides of the present invention can be in a form of DNA or RNA. DNA includes cDNA, genomic DNA, or synthetic DNA. DNA may be single-stranded or double-stranded. DNA may be the coding strand or non-coding strand.

The polynucleotide encoding the mature polypeptide of the present invention includes coding sequences encoding only mature polypeptides; coding sequences of mature polypeptides and various additional coding sequences; coding sequences (and optional additional coding sequences) of mature polypeptides and non-coding sequences.

The term "polynucleotide encoding the polypeptide" may be a polynucleotide that encodes the polypeptide, or a polynucleotide that also includes additional coding and/or non-coding sequences.

The present invention also relates to a polynucleotide that hybridize to the sequence described above and that have at least 50%, preferably at least 70%, more preferably at least 80% identity between the two sequences. In particular, the present invention relates to a polynucleotide that is hybridizable to the polynucleotide of the invention under stringent conditions. In the present invention, "stringent conditions" means: (1) hybridization and elution at lower ionic strength and higher temperature, such as 0.2×SSC, 0.1% SDS, 60° C.; or (2) hybridization in the presence of a denaturant such as 50% (v/v) formamide, 0.1% calf serum/0.1% Ficoll, 42° C. or the like; or (3) hybridization occurs only if the identity between the two sequences is at least 90%, more preferably 95% or more. And the polypeptide encoded by the hybridizable polynucleotide has the same biological function and activity as the mature polypeptide shown in one of SEQ ID NO: 32-37.

The full-length nucleotide sequence of the present invention or a fragment thereof can usually be obtained by the methods include but are not limited to PCR amplification, recombination or synthetic methods. A viable approach is to synthesize the relevant sequence in a synthetic manner, especially when the fragment length is short. In general, a very long fragment can be obtained by first synthesizing multiple small fragments and then ligating them. In addition, the coding sequence of the heavy chain and the expression tag (e.g., 6His) can be fused together to form a fusion protein.

Once the relevant sequence is obtained, the relevant sequence can be obtained in bulk using the recombination method. It is usually cloned into a vector, transferred to a cell, and then isolated from the host cell after proliferation by conventional methods. The biomolecules (nucleic acids, proteins, etc.) involved in the present invention include biomolecules present in separate form.

At present, DNA sequences encoding the protein of the invention (or fragments thereof, or derivatives thereof) can be completely obtained by chemical synthesis. The DNA sequence can then be introduced into a variety of existing DNA molecules (or vectors) and cells known in the art. In addition, mutations can also be introduced into the protein sequences of the present invention by chemical synthesis.

The present invention also relates to a vector comprising the suitable DNA sequence as described above and a suitable promoter or control sequence. These vectors can be used to transform suitable host cells to enable them to express proteins.

Host cells can be prokaryotic cells, such as bacterial cells; or lower eukaryotic cells, such as yeast cells; or higher eukaryotic cells, such as mammalian cells. Representative examples include: bacterial cells such as *Escherichia coli, Streptomyces; Salmonella typhimurium*; fungal cells such as yeast; insect cells such as *Drosophila* S2 or Sf 9; animal cells such as CHO, COST, 293 cells.

Transformation of host cells with recombinant DNA can be carried out using conventional techniques well known to those skilled in the art. When the host is a prokaryote such as *E. coli*, competent cells capable of absorbing DNA can be harvested after the exponential growth phase and treated with the $CaCl_2$. The steps used are well known in the art. Another method is using $MgCl_2$. If necessary, the transformation can also be carried out by electroporation. When the host is a eukaryote, the following DNA transfection methods are available: calcium phosphate coprecipitation, conventional mechanical methods such as microinjection, electroporation, liposome packaging, and the like.

The obtained transformants can be cultured in a conventional manner to express the polypeptides encoded by the genes of the present invention. Depending on the host cell used, the medium used in the culture may be selected from a variety of conventional media. And the host cells are cultured under conditions suitable for the growth. After the host cells grow to the appropriate cell density, the selected promoter is induced with a suitable method, such as temperature conversion or chemically induced, and the cells are cultured for a further period of time.

The recombinant polypeptide in the above method can be expressed intracellularly, or on the cell membrane, or secreted out of the cell. If desired, recombinant proteins can be isolated and purified by various separation methods using their physical, chemical, and other properties. These methods are well known to those skilled in the art. Examples of such methods include, but are not limited to, conventional renaturation treatments, treatment with a protein precipitant (salting-out method), centrifugation, osmosis cell disruption, super-treatment, ultracentrifugation, molecular sieve chromatography (gel filtration), adsorption chromatography, ion-exchange chromatography, high performance liquid chromatography (HPLC) and various other liquid chromatography techniques and combinations of these methods.

The antibodies of the invention may be used alone or in combination with or couple with a detectable label (for diagnostic purposes), a therapeutic agent, a PK (protein kinase) modified moiety, or any combination thereof.

A detectable label for diagnostic purposes include, but are not limited to, fluorescent or luminescent labels, radiolabels, MRI (magnetic resonance imaging), or CT (computerized tomography) contrast agents, or enzymes capable of producing detectable products.

Therapeutic agents that can be associated with or coupled with the antibodies of the present invention include, but are not limited to: 1. Radioactive nuclide (Koppe, et al, 2005, *Cancer metastasis reviews* 24, 539); 2. Biological toxin (Chaudhary et al, 1989, Nature, 339, 394; Epel et al, 2002, *Cancer immunology and immunotherapy* 51, 565); 3. Cytokine such as IL-2 and the like (Gillies, et al, 1992, PNAS, 89, 1428; Card, et al, 2004, *Cancer immunology and immunotherapy* 53, 345; Halin, et al, 2003, *Cancer research* 63, 3202); 4. Gold nano-particle/nano-rod (Lapotko, et al, 2005, *Cancer letters* 239, 36; Huang, et al, 2006, *Journal of the American chemical society* 128, 2115); 5. Virus particles (Peng, et al, 2004, *Gene therapy*, 11, 1234); 6. Liposome (Mamot, et al, 2005, *Cancer research* 65, 11631); 7. Magnetic nano-particles; 8. Prodrug activating enzymes (such as DT-diaphorase(DTD) or Biphenyl hydrolase-like protein (BPHL)); 10. Chemotherapeutic agent (e.g., cisplatin) or any form of nanoparticles and the like.

The present invention also provides a composition. In a preferred embodiment, the composition is a pharmaceutical composition comprising the above-described antibody or active fragment thereof or a fusion protein thereof, and a pharmaceutically acceptable carrier. In general, these materials may be formulated in a non-toxic, inert and pharmaceutically acceptable aqueous carrier medium, wherein the pH is generally about 5 to 8, preferably about 6 to 8, although the pH may vary depending on the nature of the substance to be formulated, and the condition to be treated. The formulated pharmaceutical compositions may be administered by conventional routes, including, but not limited to, intratumoral, intraperitoneal, intravenous, or local drug delivery.

The pharmaceutical compositions of the present invention can be used directly in combination with CD7 protein molecules and are therefore useful for the prevention and treatment of tumors. In addition, other therapeutic agents may be used at the same time.

The pharmaceutical composition of the present invention contains a nano-antibody (or a conjugate thereof) of the present invention in a safe and effective amount (e.g., 0.001 to 99% by weight, preferably 0.01 to 90% by weight, more preferably 0.1 to 80% by weight) and an acceptable carrier or excipient. Such carriers include, but are not limited to, saline, buffer, glucose, water, glycerol, ethanol, and combinations thereof. The pharmaceutical preparation should match the method of administration. The pharmaceutical compositions of the present invention may be prepared into the form of injections, for example, saline or aqueous solutions containing glucose and other adjuvants are prepared by conventional methods. Pharmaceutical compositions such as injections, solutions should be made under aseptic conditions. The amount of the active ingredient is a therapeutically effective amount, such as about 1 microgram/kg body weight per day to about 5 mg/kg body weight per day. In addition, the polypeptides of the present invention may also be used with other therapeutic agents.

When a pharmaceutical composition is used, a safe and effective amount of an immunoconjugate is administered to a mammal wherein the safe effective amount is generally at least about 10 micrograms per kilogram of body weight and, in most cases, no more than about 8 milligrams per kilogram of body weight, preferably, the dose is from about 10 micrograms per kilogram body weight to about 1 milligram per kilogram of body weight. Of course, the route of administration, the patient's health and other factors, should be considered for the specific dose, which are within the scope of skills of skilled practitioners.

Labeled Immunoglobulin

In a preferred embodiment of the invention, the Nanobody has a detectable label. Preferably, the label is selected from the group consisting of a colloidal gold label, a colored marker and a fluorescent label.

Colloidal gold labels can be carried out using methods known to those skilled in the art. In a preferred embodiment of the invention, the monoclonal antibody of the CD7 protein is labeled with colloidal gold to obtain a colloidal gold-labeled monoclonal antibody.

The CD7 protein monoclonal antibody of the invention has good specificity and high titer.

Methods and Samples

The present invention relates to a method for detecting a CD7 protein in a sample having dissolved cells and/or tissues. Steps of the method are basically as follows: obtaining a cell and/or tissue sample; dissolving the sample in a medium; detecting the level of CD7 protein in the dissolved sample. The sample used in the method of the present invention may be any sample in the cell preservation solution containing the cells, as used in liquid-based cell assays.

Kit

The present invention also provides a kit for containing an antibody (or a fragment thereof) or a detection plate of the present invention. In a preferred embodiment of the present invention, the kit further comprises a container, an instruction for use, a buffer agent and so on.

A detection kit is further designed according to the present invention for detecting CD7 levels, said kit contains antibodies that recognize the CD7 protein, a lysis medium for dissolving the sample, general reagents and buffers desired for detection, such as various buffers, detection labels, detection substrates and so on. The assay kit may be an in vitro diagnostic device.

Materials and Method

Strains and Plasmids

*Escherichia coli* TOP10 was used to amplify the plasmids and clones. *Escherichia coli* XL1-Blue (Stratagene) was used to amplify the library of the phage antibodies, and *E. coli* BL-21 (DE3) was used to express the proteins. The phage plasmid pCOMB 3XSS was used to prepare the phage library, pcDNA3.1 was used to construct the eukaryotic expression plasmid, and pET28a was used for prokaryotic expression. Lentiviral vector Red-OG2 was used to construct stable cell lines.

2. Patient Samples and Cell Lines

After approved by the Ethics Committee, the blood or the bone marrow of T-ALL and T-AML patients was extracted to prepare primary cells. Mononuclear cells were isolated by Ficol according to the standard procedures. Primary cells were cultured with RPMI1640 medium with 20% FBS supplemented with the double-antibody.

Leukemia cell line Jurkat, CEM, and lung cancer cell line H460 were cultured with RPMI1640 medium with 10% FBS and the double-antibody was added. The myeloma cell lines RPMI8226 were cultured using IMDM medium with 10% FBS and a double antibody was added. 293T cell lines were cultured using 10% FBS DMEM medium and a double antibody was added.

3. Nanobody Screening

CD7-positive Jurkat cells were used to immunize camels, camel peripheral blood was extracted and the RNAs were extracted to establish a phage antibody library. The CD7-specific Nanobody was screened by cell-washing method. The brief procedure was as follows: 293T-CD7 stable cell lines were constructed by lentivirus transfection. The freshly prepared phage nano-antibody suspension was washed on 293T and 293T-CD7 cells. After three rounds of screening, monoclonal was picked and then 293T and 293T-CD7 cells were subjected to whole-cell enzyme-linked immunosorbent assay. Positive clones were screened for sequencing.

4. The Expression and Purification of CD7 Nanobodies

The obtained positive clone nanoclonal antibody sequence was cloned into the prokaryotic expression vector pET28a, and the His tag and HA tag at the C-terminus were used for purification and identification, and then the product was transformed into the expression strain BL-21, and induced by IPTG. The purified nanobodies were obtained by affinity purification. The protein purity was identified by Coomassie brilliant blue staining. The protein concentration was detected by BCA method.

5. The Construction, Expression and Purification of CD7 Nanobody Immunotoxins

The whole gene of truncated Pseudomonas toxin PE38 and nano-antibody VHH-6 were synthesized and inserted into a pET28a vector and a 6-His tag at the N-terminus was used for purification and detection. The product was also transformed into the expressed strain BL-21, and induced by IPTG for expression. The nanobody immunotoxins expressed by prokaryotes were purified by affinity purification to yield purified nanobodies. The purity of the protein was identified by Coomassie brilliant blue staining. The protein concentration was detected by BCA method. The divalent immunotoxin was constructed as the monovalent immunotoxin was by being inserted into the VHH-6 sequence before the VHH-6 sequence through PCR, and the prokaryotic expression is carried out, followed by purification and identification.

6. The Affinity of the Nanobodies of the Present Invention was Determined:

The protocol was as follows: to assess the affinity of the selected Nanobodies, Jurkat cells were incubated on ice with different concentrations of Nanobodies and were washed twice with PBS and then were incubated with APC-labeled anti-HA monoclonal antibodies (Miltenyi Biotec, CHN) on ice in the PBS containing 2% BSA for 1 h. After washing twice with PBS, fluorescence intensity was detected using FACSCalibur. The binding saturation curve, the nonlinear regression curve, and the Scatchard plots were prepared using the software Graph Pad Prism (Graph Pad Software, Inc).

7. Flow Analysis

The binding specificity of the Nanobodies and Nanobody immunotoxins was detected by flow cytometry. Approximately $3 \times 10^5$ cells (Jurkat, CEM, H460, RPMI8226) were washed twice with PBS and resuspended in the Nanobodies with a final concentration of 5 μg/ml and the 50 μL PBS containing Nanobody Immunotoxin, respectively. The product was placed on ice for 1 hour, washed twice with PBS, resuspended in PBS after adding 1 μg of anti-HA sheep polyclonal antibodies or anti-His mouse monoclonal antibodies, and placed on ice for 1 hour. And then the cells were washed twice, and incubated with anti-sheep monoclonal antibody Alexa488 (CST) and anti-mouse monoclonal antibody Alexa647 (CST) respectively on ice for 1 hour. And finally the cells were washed three times with PBS for flow detection. The CD7 expression level of Lipo2000 transfected pcDNA3.1-CD7 lung cancer cell line H460 was determined with commercial antibodies using flow cytometry. Approximately $3\times10^5$ transfected cells were washed twice with PBS and incubated with commercial antibodies (BD CD7-PE) on ice for 1 hour, washed twice with PBS, and finally subjected to flow cytometry.

8. Cell Immunofluorescence

The specificity of the nanobodies was detected by cellular immunofluorescence.

Jurkat and RPMI8226 cells were inoculated in a six-well plate containing poly-lysine-treated slides and incubated overnight at 37° C. The glass slide was removed, washed twice with PBS and fixed with 4% paraformaldehyde for 15 minutes, and then blocked with 3% BSA for 1 hour. And finally the nanometer antibodies was added and incubated at room temperature for 1 hour, washed twice with PBS. The anti-HA sheep polyclonal antibodies were added, incubated for 1 hour at room temperature, and washed twice with PBS. Thereafter, anti-sheep monoclonal antibodies Alexa488 (CST) were added, incubated for 1 hour at room temperature, washed three times with PBS and pictured with confocal fluorescence microscopy.

Lipo2000 was transfected into H460 cells of pcDNA3.1 and pcDNA3.1-CD7, respectively, and immunofluorescence was detected in the same manner as above.

9. The Cytotoxic Effects of the CD7-Nanobody Immunotoxin

The concentration-dependent cytotoxicity effects of the Nanobody immunotoxins against the target cells were determined by the WST-8 kit.

Cells were seeded at $1\times10^4$ cells/well (wherein H460 cells were seeded at $3\times10^3$) in a 96-well plate incubated with different concentrations of immunotoxins. After 72 hour, 10 μl of WST-8 reagent was added, and the product was incubated at 37° C. until the maximum absorbance was read out. In order to detect whether the cell growth inhibition caused by the immunogenicity of the nanobody antibody was caused by apoptosis, $2.5\times10^5$ cells were added to the 24-well plate and 150 ng/ml of toxin was added. After treated for different times, the treated cells were stained with FITC-labeled Annexin V and 7-AAD, according to the kit instruction. The blocking test was performed by adding 50-fold of the parent antibody 1 hour before the addition of the monovalent immunotoxin (150 ng/ml).

10. Polyacrylamide Gel Electrophoresis and Immunoblotting

SDS-PAGE experiments were carried out according to the standard experimental procedures. The gel was stained with Coomassie Brilliant Blue R-250. HRP-labeled secondary antibody was used in immunoblotting. Enhanced luminescence kits were used for detection. Nanobody immunotoxins were detected by anti-His tag. Full length PARP and its specific shear products were detected with rabbit anti-human PARP antibodies.

11. Antitumor Activity of the Toxins in NOD/SCID Mice

CEM cells were washed once with PBS, and on day 0, each NOD/SCID mouse was injected with $2\times10^6$ CEM cells through the tail vein. On day 5, 5 μg of PG001 was injected into each mouse, and administered once every other day for 3 times. The daily health status of mice was monitored. Dying mice are killed according to the procedure. The survival time of mice was assessed by Karl-Meyer to assess the therapeutic effect of toxins and to detect median survival.

The Main Advantages of the Present Invention Comprise:
(1) The anti-CD7 protein nanobody of the present invention has high specificity, strong affinity, good thermal stability, and can be prepared in large quantities, and the quality is easily controlled.
(2) The anti-CD7 protein nanobody of the present invention can efficiently induce apoptosis of CD7-positive T lymphocytic leukemia cell line by coupling Pseudomonas exotoxin.

The invention will now be further described with reference to specific examples.

Example 1: Construction of Nanobody Library Against Human CD7

(1) The immunization of the camels with CD7 over expressed cell lines: a Xinjiang bactrian camel (Dazhong Breeding group co., LTD) was immunized with $5\times10^6$ CD7 overexpressing Jurkat cell lines (purchased from ATCC) once a week for continuous immunization for 7 times. B cells were stimulated to express antigen-specific Nanobodies in the immunization process. (2) At the end of 7 times immunizations, 50 ml of camel peripheral blood lymphocytes were extracted and the total RNA was extracted (Trizol method). (3) According to the instruction of Thermo Scientfic K1621\K1622 kit, the extracted RNA was reverse transcribed into cDNA and then the VHH chain was amplified by PCR. The first round of PCR:

```
Upstream primer:
                                   (SEQ ID NO.: 45)
GTCCTGGCTCTCTTCTACAAGG Downstream primer:
                                   (SEQ ID NO.: 46)
GGTACGTGCTGTTGAACTGTTC
```

The fragment between the signal peptide of antibody heavy chain and the antibody CH2 was amplified, annealed at 55° C. for 32 cycles. Agarose gel electrophoresis was used to recover DNA fragments with a size of 650 bp to 750 bp as shown in FIG. 1.

The Second Round of PCR:

The products of first round PCR was used as a template,

```
Upstream primer:
                                   (SEQ ID NO.: 47)
CGAGCTCATGGATGTGCAGCTGCAGGAGTCTGGAGGAGG Downstream primer:
                                   (SEQ ID NO.: 48)
GGACTAGTGATGGAGACGGTGACCTGGGT
```

Figure 2:
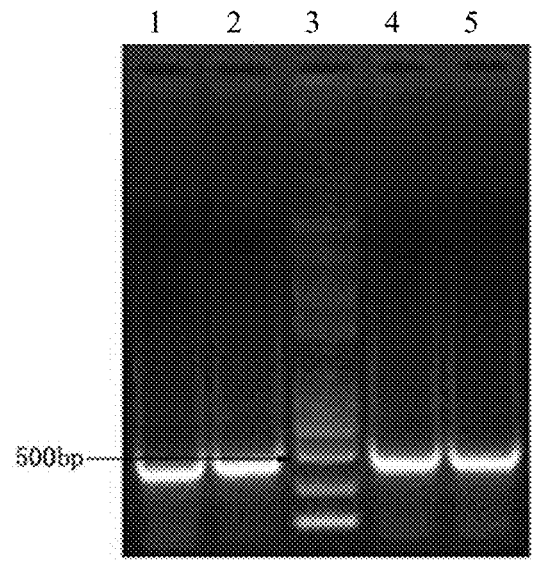
FIG. 2 shows an agarose gel electrophoresis of the second round PCR products. Fragments of about 500 bp are excised from the gel and recovered. Lane 3 is DNA marker, the other lanes shows DNA fragments of variable region fragments of heavy chain antibodies.
Figure 3:
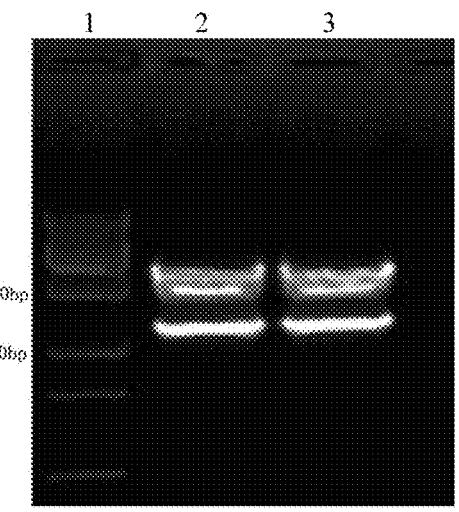
FIG. 3 shows an agarose gel electrophoresis of SpeI and SacI double-digested phage vector pComb3XSS. Fragments of about 3200 bp are excised from the gel and recovered. Lane 1 is DNA marker, and both Lane 2 and Lane 3 are loaded with samples of double-digested phage vector pComb3XSS.
Figure 10:
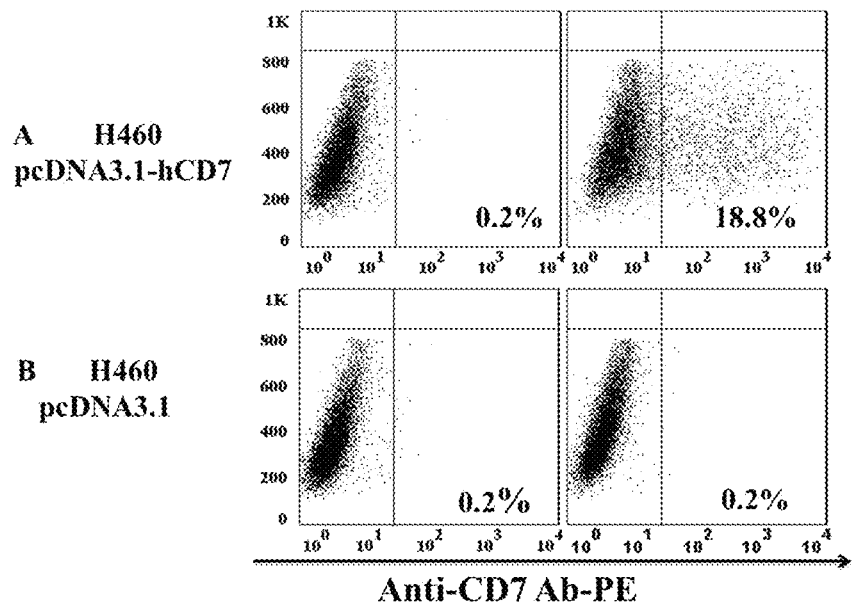
FIG. 10 shows results of flow cytometry assay of a CD7 negative cell line H460 transfected with pcDNA3.1-hCD7 or pcDNA3.1 and stained with commercial anti-CD7 Ab-PE.

The FR1 and FR4 regions of the antibody heavy chain were amplified, annealed at 61° C., 35 cycles. The target fragment with a size of about 500 bp was recovered, and the result was shown in FIG. 2. (4) the restriction endonucleases (purchased from NEB) Spe I and Sac I were used to digest 10 μg of pComb3XSS phage display vector (purchased from Creative Biogene) as shown in FIG. 3, and 10 μg of VHH was double digested. The two fragments were ligated by T4

Figure 4:
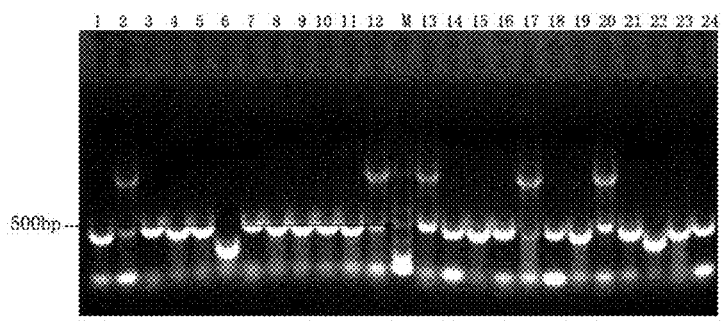
FIG. 4 shows an agarose gel electrophoresis of colony PCR of 24 randomly selected clones. Lane M is DNA marker, and the other lanes are loaded with samples of colony PCR of 24 randomly selected clones.

DNA ligase (purchased from NEB). (5) The ligation product was purified and electrotransformed into the electro-transgenic competent cell XL1-Blue (purchased from 2ndLab™) to construct the CD7 Nanobody phage display library and the storage capacity was determined as about $7.3 \times 10^7$. At the same time, colony PCR was used to detect the insertion rate of the constructed library. FIG. 4 showed the colony PCR results. 24 clones were randomly selected for colony PCR and the results showed that the insertion rate was 96%.

Example 2: Screening Process of Nanobody Against CD7

(1) 3% BSA\PBS was added into 293T cells, and incubated at room temperature for 30 min. 3% BSA/PBS was removed and the cells were washed twice with PBS. Freshly prepared phage nanobody suspension was added immediately and incubated at 37° C. for 1 hour while slightly shaking the dishes. (2) 3% BSA\PBS was added into 293T-CD7$^+$ cells, and incubated at room temperature for 30 min. After removing 3% BSA\PBS, the cells were washed twice with PBS and the supernatant from (1) was added immediately and then incubated at 37° C. for 1 hour while slightly shaking the dishes. (3) The supernatant was removed and the cells were collected and washed three times with PBS\Tween-20, and then the glycine-hydrochloric acid elution buffer (pH 2.2) was added to the cells. The cells were incubated at 37° C. for 30 min, Tris\HCl buffer (pH 7.4) was added in proportion, and pH was neutralized. Centrifugation was conducted for removing the cells, and the phage suspension was contained in the supernatant. (4) The phage suspension in the previous step was used to infect the XL1-Blue *Escherichia coli* in the logarithmic growth phase. The phages were produced and purified for the next round of cell screening. After three rounds, the phage was gradually screened.

Example 3: Single Specific Positive Clones (Whole Cell ELISA) were Screened by Enzyme-Linked Immunosorbent Assay (ELISA) of Phage 1. Expression of Phage Antibodies in Microtiter Plates 32 individual clones were picked with a sterile toothpick and placed into a 96-wells microtiter plate containing 100 μl of 2×TY/amp/glu per well and incubated overnight with shaking (300 r/min) on a microtiter plate shelf (2) 50 μl of 2×TY/amp/glu/gly was added into each well and stored at −70° C. (3) Using a sterile 96-well transfer device or pipette, 2 μl of liquid was drawn from each well of the main plate and inoculated into a 96-well plate containing 150 μl of 2×TY/amp/glu per well and shaked at 37° C. until the A600 value was close to 0.5 (2.5 hours); (4) 50 μl of 2×TY/amp/glu containing $2 \times 10^9$ pfu/ml auxiliary phage (diluted in stock solution) was added, and the ratio of phage to bacteria was close to 20:1. The plate was incubated at 37° C. for 30 minutes. (5) The plate was centrifuged at 2700 r/min for 10 minutes, and the supernatant was removed by multichannel pipettes or draining device. (6) The bacterial pellet was precipitated with 150 μl of 2×TY/amp/kan to allow the phage Nanobody to be expressed and the plate was incubated at 37° C. with shaking (300 r/min) overnight. (7) The next day, the plate was centrifuged at 2700 r/min for 10 minutes and 50 μl of supernatant per well was sucked for phage ELISA.

1. Whole Cell ELISA

Figure 5:
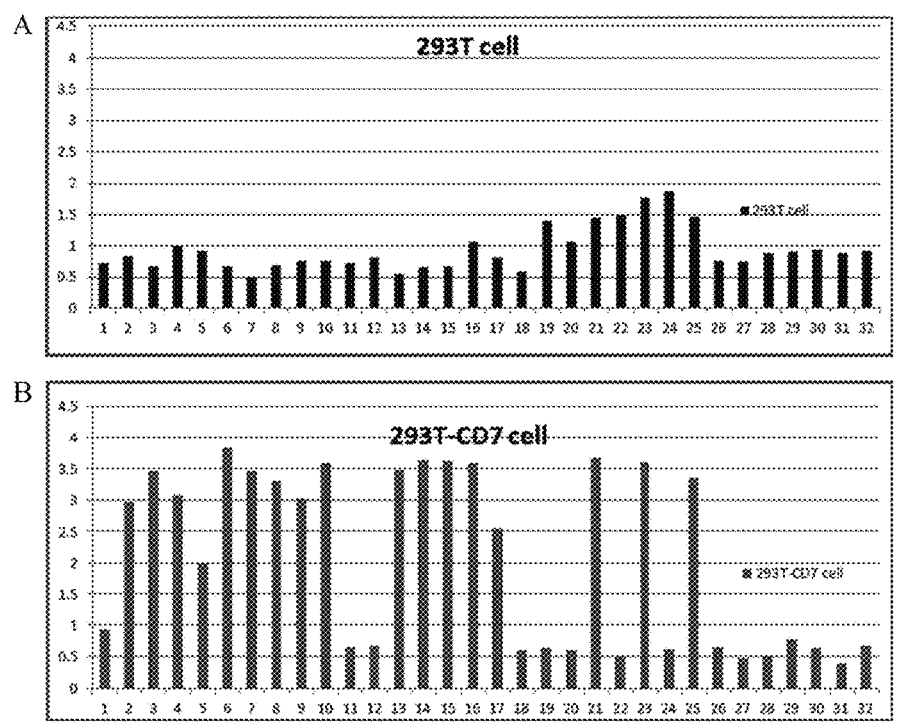
FIG. 5 schematically illustrates screening results of specific single positive clones on a cell using an enzyme-linked immunoassay (ELISA) of phage.

293T-CD7+ cells ($5 \times 10^5$ cells) and 293T-CD7-cells ($5 \times 10^5$ cells) were added to a 96-well plate, and 50 μl of each phage suspension was taken and added into the 96-well plate and numbered correspondingly. The 96-well plate was incubated at room temperature for 1 h and centrifuged to remove the supernatant. Each well was washed twice with PBS. (2) HRP-labeled anti-HA-Tag antibodies were added to each well, the product was incubated at room temperature for 1 h and centrifuged to remove the supernatant. The cells were washed with PBS for three times and the supernatant was thoroughly removed. A TMB color development method was used for coloration. (3) The plate was subjected to reading at 450 nm with a microplate reader and the data was stored. (4) The data was processed and the experimental results were analyzed. (5) When the OD value of the sample is 2.5 times greater than the OD value of control well, the clone was judged as a positive clone as the results shown in FIG. 5. (6) The bacteria in the corresponding positive clone wells were shaken into a medium containing 3 ml of LB Liquid to extract the plasmid and perform sequencing analysis.

The sequence alignment software DNAMAN was used to analysis of the gene sequence of each clone. The strains having the same CDR1, CDR2, CDR3 sequences were regarded as the same clones, and the strains with different sequences were regarded as different clones. Finally, a total of 6 strains with high affinity and high specific were obtained.

The sequences information of preferred clone screened by the present invention is as follows:

```
Clone 1:
The amino acid sequence is
                                                            (SEQ ID NO.: 32)
MDVQLQESGG GSVQAGGSLR LSCPASGYTF SHYCMGWNRQ APGKEREEVA TIDTDDTPTY    60

ADSVMGRFTI SRDNANNALY LQMNDLKPED TSMYYCAIWM KLRGSCHDRR LEVRGQGTQV   120

TVSIN                                                              125

The encoded nucleotide sequence is
                                                            (SEQ ID NO.: 38)
atggatgtgc agctgcagga gtctggagga ggctcggtgc aggctggagg gtctctgaga    60
ctctcctgtc cagcctctgg atacaccttc agtcactact gcatgggctg gaaccgccag   120
gctccaggaa aggagcgcga ggaggtcgcg actattgata ctgatgatac cccaacctac   180
gcagactccg tgatgggccg attcaccatc tccagagata cgccaacaa cgctctgtat    240 ctgcaaatga acgacctgaa acctgaggac acttccatgt actactgtgc gatttggatg   300
```

-continued

```
aaattgcgag gtagctgcca cgataggcgt ctcgaagttc ggggccaggg cacccaggtc    360
accgtctcca tcaactag                                                  378
```

Clone 2:
The amino acid sequence is
(SEQ ID NO.: 33)

```
MDVQLQESGG GSVQAGGSLR LSCAASGYTH SSYCMAWFRQ APGREREGVA SIDSDGTTSY     60

ADSVKGRFTI SQDNAKNTLY LQMNSLKPED TAMYYCAARF GPMGCVDLST LSFGHWGQGT    120

QVTVSIT                                                              127
```

The encoded nucleotide sequence is
(SEQ ID NO.: 39)

```
atggatgtgc agctgcagga gtctggggga ggctcggtgc aggctggagg gtccctgaga     60
ctctcctgtg cagcctctgg atacacccac agtagttact gcatggcctg gttccgccag    120
gctccaggga gggagcgcga gggggtcgca tctattgata gtgacggtac acaagctac    180 gcagactccg tgaagggccg attcaccatc tcccaagaca cgccaagaa cacgctgtat    240 ctgcaaatga acagcctgaa acctgaggac actgccatgt actactgtgc ggcccgattt    300
gggcctatgg gttgtgtaga cctcagtacg ttgagctttg ggcactgggg ccaggggacc    360
caggtcaccg tctccatcac ttag                                           384
```

Clone 3:
The amino acid sequence is
(SEQ ID NO.: 34)

```
MDVQLQESGG GSVQAGGSLR LSCPASGYTF SHYCMGWLRQ APGKEREEVA TIDTDSTPTY     60

ADSVMGRFTI SRDNANNALY LQMNDLKPED TSMYYCATWM GLRGSCHDRR LEVRGQGTQV    120

TVSIN                                                                125
```

The encoded nucleotide sequence is
(SEQ ID NO.: 40)

```
atggatgtgc agctgcagga gtctggagga ggctcggtgc aggctggagg gtctctgaga     60
ctctcctgtc cagcctctgg atacaccttc agtcactact gcatggggttg ctccgccag    120 gctccaggaa aggagcgcga ggaggtcgcg actattgata ctgatagtac ccaacctac    180 gcagactccg tgatgggccg attcaccatc tccagagata cgccaacaa cgctctgtat    240 ctgcaaatga acgacctgaa acctgaggac acttccatgt actactgtgc gacttggatg    300
ggattgcgag gtagctgcca cgacaggcgt ctcgaagttc ggggccaggg cacccaggtc    360
accgtctcca tcaactag                                                  378
```

Clone 4:
The amino acid sequence is
(SEQ ID NO.: 35)

```
MDVQLQESGG GSVQAGGSLR LSCAASGYTT SRLCMAWFRQ FPGKEREGVA NVRLGGYKPA     60

YADSVKGRFT LSEDSAKNTV YLEMNSLQPE DTAMYYCAAD PGGGGSCPVA LVRGDFDYWG    120

QGTQVTVSIN                                                           130
```

The encoded nucleotide sequence is
(SEQ ID NO.: 41)

```
atggatgtgc agctgcagga gtctggagga ggctcggtgc aggctggagg gtctctgaga     60
ctctcctgtg cagcctctgg atacaccacc agtcgccttt gcatggcctg gttccgccag    120
tttccaggga aggagcgcga ggggtcgcg aatgttaggc ttggtggtta taagccagcc    180
tatgccgact ccgtgaaggg ccgattcacc ctctccgaag acagcgccaa gaacacggtg    240
tatctcgaaa tgaacagcct ccaacctgag acactgcca tgtattactg cggcagat    300 cccggggggcg gtggtagctg tccggtcgcc ctagttcgag gtgactttga ttactggggc    360
caggggaccc aggtcaccgt ctccatcaac tag                                 393
```

-continued

Clone 5:
The amino acid sequence is
(SEQ ID NO.: 36)

MDVQLQESGG GLVQAGGSLR LSCAVSGYPY SSYCMGWFRQ APGKEREGVA AIDSDGRTRY    60

ADSVKGRFTI SQDNAKNTLY LQMNRMKPED TAMYYCAARF GPMGCVDLST LSFGHWGQGT   120

QVTVSIT                                                             127

The encoded nucleotide sequence is
(SEQ ID NO.: 42)
atggatgtgc agctgcagga gtctggagga ggcttggtgc aggctggagg gtctctgaga    60
ctctcctgtg cagtctctgg atacccctac agtagctact gcatgggctg gttccgccag   120
gctccaggga aggagcgcga gggggtcgct gctattgata gtgatggtag acaaggtac    180
gcagactccg tgaagggccg attcaccatc tcccaagaca cgccaagaa cactctgtat   240
ctgcaaatga acagaatgaa acctgaggac actgccatgt actactgtgc ggcccgattt    300
gggcctatgg gttgtgtaga cctcagtacg ttgagctttg gcactgggg ccaggggacc    360
caggtcaccg tctccatcac ttag                                          384

Clone 6:
The amino acid sequence is
(SEQ ID NO.: 37)

MDVQLQESGG GSVQAGGSLR LSCAASGYTY STYCMGWFRQ APGKEREGVA TIDSDGSTSY    60

ADSVKGRFTI SRDNAKNTLN LQMSSLKPED TAMYYCAARF GPMGCVDLST LSFGHWGQGT   120

QVTVSIT                                                             127

The encoded nucleotide sequence is
(SEQ ID NO.: 43)
atggatgtgc agctgcagga gtctggagga ggctcggtgc aggctggagg gtctctgaga    60
ctctcctgtg cagcctctgg atacacctac agtacgtact gcatgggctg gttccgccag   120
gctccaggaa aggagcgcga gggggtcgca actattgata gtgatggtag cacaagctac   180
gcagactccg tgaagggccg attcaccatc tccagagaca cgccaagaa cactctgaat   240
ctacaaatga gcagcctgaa acctgaggac actgccatgt actactgtgc ggcccgattt    300
gggcctatgg gttgtgtaga cctcagtacg ttgagctttg gcactgggg ccaggggacc    360
caggtcaccg tctccatcac tagt                                          384

TABLE II

The preferred clone sequence information screened in the present invention

| Clone NO. | Sequence | SEQ ID NO: |
|---|---|---|
| 1 | FR1 MDVQLQESGG GSVQAGGSLR LSCPAS | 1 |
|   | CDR1 GYTFSHYCM | 17 |
|   | FR2 GWNRQAPGKE REEVA | 2 |
|   | CDR2 TIDTDDTPT | 18 |
|   | FR3 YADSVMGRFT ISRDNANNAL YLQMNDLKPE DTSMYYC | 3 |
|   | CDR3 AIWMKLRGSC HDRRLEVR | 19 |
|   | FR4 GQGTQVTVSI N | 4 |
| 2 (VHH-10) | FR1 MDVQLQESGG GSVQAGGSLR LSCAAS | 5 |
|   | CDR1 GYTHSSYCM | 20 |
|   | FR2 AWFRQAPGRE REGVA | 6 |
|   | CDR2 SIDSDGTTS | 21 |
|   | FR3 YADSVKGRFT ISQDNAKNTL YLQMNSLKPE DTAMYYC | 7 |
|   | CDR3 AARFGPMGCV DLSTLSFGH | 22 |
|   | FR4 WGQGTQVTVS IT | 8 |

TABLE II-continued

The preferred clone sequence information screened in the present invention

| Clone NO. | Sequence | SEQ ID NO: |
|---|---|---|
| 3 | FR1 MDVQLQESGG GSVGAGGSLR LSCPAS | 1 |
|   | CDR1 | 17 |
|   | FR2 GWLRQAPGKE REEVA | 9 |
|   | CDR2 TIDTDSTPT | 23 |
|   | FR3 YADSVMGRFT ISRDNANNAL YLQMNDLKPE DTSMYYC | 3 |
|   | CDR3 ATWMGLRGSC HDRRLEVR | 24 |
|   | FR4 GQGTQVTVSI N | 4 |
| 4 | FR1 MDVQLQESGG GSVGAGGSLR LSCAAS | 5 |
|   | CDR1 GYTTSRLCM | 25 |
|   | FR2 AWFRQFPGKE REGVA | 10 |
|   | CDR2 NVRLGGYKPA | 26 |
|   | FR3 YADSVKGRFT LSEDSAKNTV YLEMNSLQPE DTAMYYC | 11 |
|   | CDR3 AADPGGGSC PVALVRGDFD Y | 27 |
|   | FR4 WGQGTQVTVS IN | 12 |

TABLE II-continued

The preferred clone sequence information
screened in the present invention

| Clone NO. | | Sequence | SEQ ID NO: |
|---|---|---|---|
| 5 (VHH-6) | FR1 | MDVQLQESGG GLVQAGGSLR LSCAVS | 13 |
| | CDR1 | GYPYSSYCM | 28 |
| | FR2 | GWFRQAPGKE REGVA | 14 |
| | CDR2 | AIDSDGRTR | 29 |
| | FR3 | YADSVKGRFT ISQDNAKNTL YLQMNRMKPE DTAMYYC | 15 |
| | CDR3 | AARFGPMGCV DLSTLSFGH | 22 |
| | FR4 | WGQGTQVTVS IT | 8 |
| 6 | FR1 | MDVQLQESGG GSVGAGGSLR LSCAAS | 5 |
| | CDR1 | GYTYSTYCM | 30 |
| | FR2 | GWFRQAPGKE REGVA | 14 |
| | CDR2 | TIDSDGSTS | 31 |
| | FR3 | YADSVKGRFT ISRDNAKNTL NLQMSSLKPE DTAMYYC | 16 |
| | CDR3 | AARFGPMGCV DLSTLSFGH | 22 |
| | FR4 | WGQGTQVTVS IT | 8 |

Figure 6:
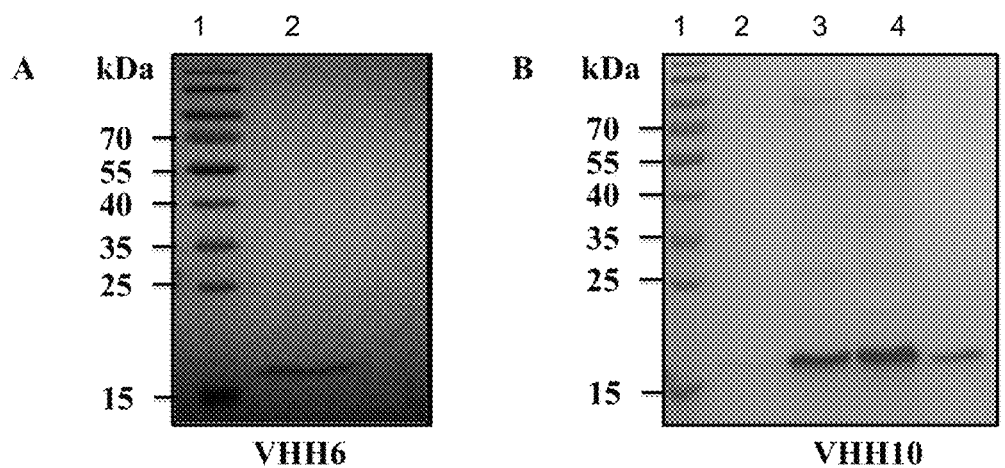
FIG. 6 shows Coomassie brilliant blue stained SDS-PAGE of 4 nanobody samples purified by Ni-ion affinity chromatography after prokaryotic expression (clone VHH6 and clone VHH10).

Example 4: The Expression and Purification of the Nanobody in *E. coli* Host Cells (1) Six kinds of nanobodies obtained by the previous sequencing analysis were subcloned into the expression vector PET27b (+), and the correct recombinant plasmid was transformed into the expression-type host strain BL (DE3) and coated to a LB solid medium plate containing 50 µg/ml of kanamycin and incubated overnight at 37° C. (2) The single colony was picked and inoculated in 3 ml of LB medium containing kanamycin and incubated overnight at 37° C. with shaking. (3) 1 ml of the overnight strain was inoculated into 250 ml of LB medium and incubated at 37° C. in a shaking culture to the OD value reached 0.6 to 1, and IPTG was added. The product was incubated overnight at 37° C. (4) The next day, cells were collected by centrifugation. (5) The cells were disrupted to obtain an antibody crude extract. (6) The antibody proteins were purified by nickel column ion affinity chromatography to obtain the high purity nanobodies as shown in FIG. 6, which showed the Coomassie brilliant blue staining after SDS-PAGE of the 4 consecutive tubes of nanobody collected in purification of one of the nanobodies (the clone 2 antibody of the present invention, i.e., clone VHH-10). The VHH-6 clone stained with Coomassie Brilliant Blue had a band with the same size.

Figure 7:
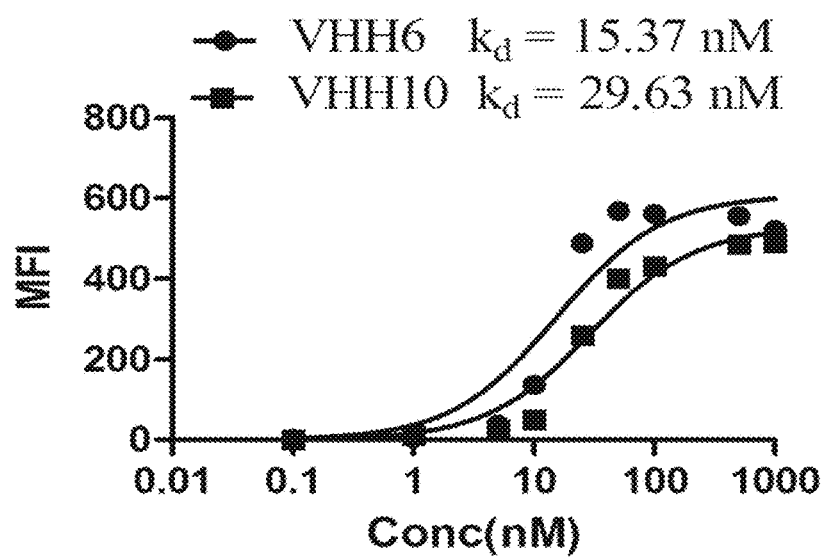
FIG. 7 shows binding curves and affinity results of nanobodies VHH6 and VHH10 with high expressing CD7 Jurkat cell lines. MIF represents the affinity of antibody.

Example 5: Analysis on the Affinity of Two Nanobodies to CD7-Positive Jurkat Cells by Flow Cytometry The results showed that the affinity of the two nanobodies VHH6 and VHH10 of the present invention was 15.37 nM and 29.63 nM, respectively, as shown in FIG. 7.

Example 6: Activity Detection of the Obtained Nanobody by Flow Cytometry

Figure 8:
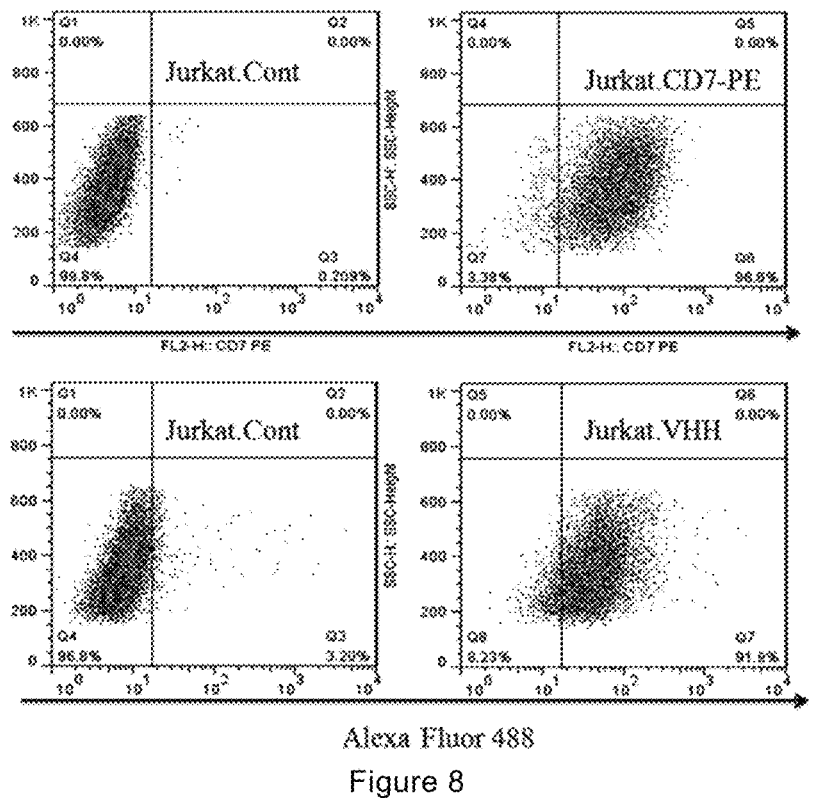
FIG. 8 shows results of flow cytometry assay of CD7 positive Jurkat cells simultaneously stained using commercially available CD7 antibodies and the obtained high-purity VHH6 nanobodies. x-axis of FIG. 8 represents the CD7 expression on Jurkat cells detected in different experimental groups, and y-axis of FIG. 8 represents the cell particle size.
Figure 9:
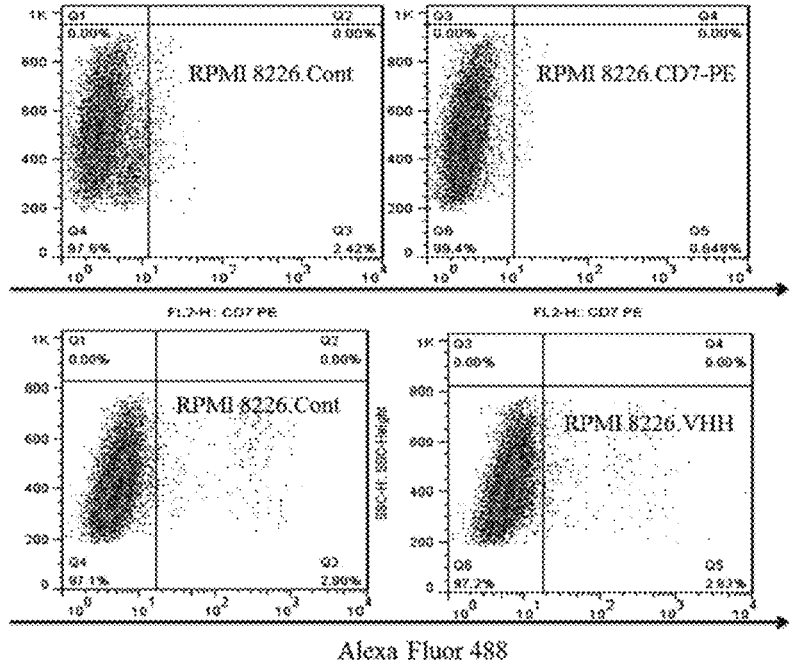
FIG. 9 shows results of flow cytometry assay of CD7 negative RPMI8226 cells simultaneously stained with commercially available CD7 antibody and the obtained high-purity VHH6 nanobody. x-axis of FIG. 9 represents the CD7 expression on RPMI8226 cells detected in different experimental groups, and y-axis of FIG. 9 represents cell particle size.

High-purity nanobodies (clone 2, i.e. clone VHH-6) were subjected to flow cytometry analysis on CD7-positive cell line Jurkat cells and compared with commercial CD7 antibody. The experimental steps were as follows: After incubation for 1 hour at room temperature, the cells were washed with PBS for 3 times, the anti-HA-tag antibodies (rabbit antibody) were added and the product incubated at room temperature for 1 hour. Then the cells were washed 3 times with PBS. The anti-rabbit Alexa Fluor® 488 fluorescent labeled antibodies were added and the product was incubated at room temperature for 1 hour, washed 3 times with PBS, and finally detected by flow cytometry. The results are shown in FIG. 8, indicating that the ratio of the obtained nanobodies binding with the positive cell was similar with that of the commercial antibodies (purchased from BD company which was a conventional monoclonal antibody, and the antibody could bind with human cells expressing CD7 molecules on the surface including tumor cells expressing CD7 molecules and primary cells with high expression of CD7 such as T lymphocytes and natural killer cells). Flow cytometry was performed on RPMI8226 cells from the CD7-negative cell line with high purity nanobodies to detect specificity. The experimental procedure was the same as above. The results were shown in FIG. 9, indicating that the obtained nanobody had a high specificity.

As could been seen from FIG. 8 of CD7+ positive cell lines (the upper left picture showed the corresponding commercial antibody staining of the control group; the right was the commercial PE labeled CD7 positive cell line (Jurkat)), the results of flow cytometry showed that the positive rate of CD7+ was 96.6%. The control group was labeled with VHH antibody (the lower left), and Jurkat was labeled with VHH-6 antibody (the lower right) and the results of flow cytometry showed that the positive rate of CD7+ was 91.8%. The positive rate of CD7+ was similar between the two groups. As in the negative cell line RPMI-8226, the positive rates of the commercial antibodies and the VHH-6 antibodies were both below 3% (0.648%, 2.82%, respectively).

Example 7: Activity Detection of the Obtained Nanobodies by Cellular Immunofluorescence The pcDNA3.1-CD7 plasmid was transfected into CD7-negative cell line H460 cells with lipofectamine2000 transfection reagent. After 48 hours, H460 cells were digested with trypsin. Half of the cells were incubated for 24 hours for flow cytometry detection (commercial antibody) for transfection effects. The other half of the cells was used for cell climbing tablets and 24 hours later, the cells were subjected to immunofluorescence detection. Flow cytometry method was as follows: the transfected H460 cells were washed with PBS for 3 times, the commercial CD7 flow cytometry antibodies were added, and the product was washed with PBS for 3 times upon an incubation at room temperature for 1 hour. The flow cytometry test results shown in FIG. 10 indicated that the transfection efficiency is about 18%. The cell immunofluorescence detection procedures were as follows: the slide was taken, washed twice with PBS and fixed with 4% paraformaldehyde for 15 minutes fixation, then blocked with 3% BSA for 1 hour, and finally stained with the antibody using the same method as in Example 5. The pictures were taken by a Confocal fluorescence microscope. The results were shown in FIG. 10 showing a similar proportion with the commercial antibody staining, and the specificity was better. Similarly, the immunofluorescence staining was performed on Jurkat cell lines expressing CD7 molecules and CD7-negative cell lines RPMI-8226. The results indicated that VHH6 could specifically bind to Jurkat cells while no fluorescence was detected on the surface of RPMI-8226 cells.

Figure 11:
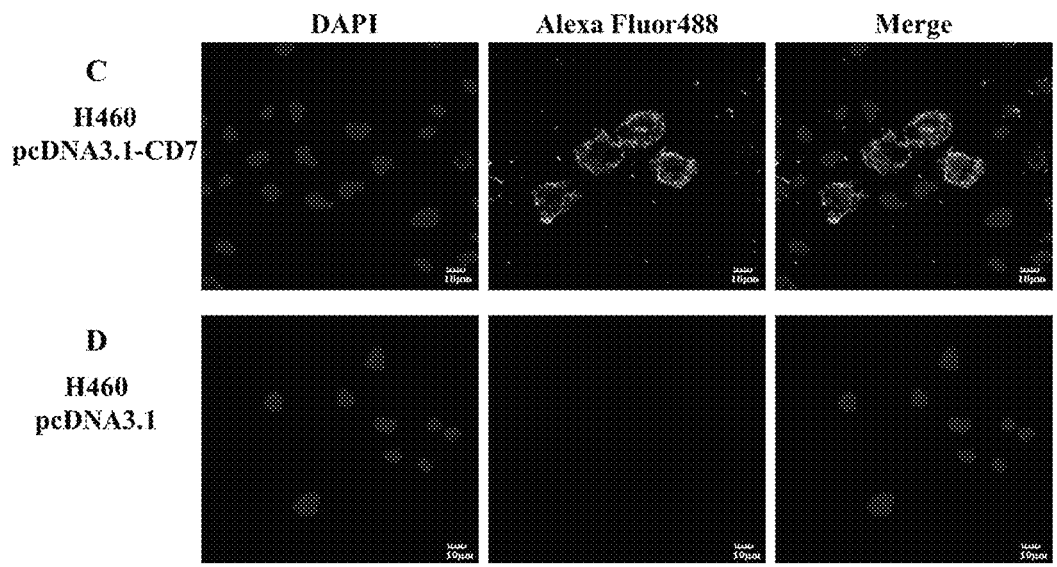
FIG. 11 shows confocal fluorescence microscopy image of H460 cells transfected with CD7, stained using the obtained high-purity VHH6 nanobodies, and subjected to the cellular immunofluorescence assay, H460 cells were transfected with pcDNA3.1-CD7 and empty vector pcDNA3.1 respectively, then incubated with VHH6 antibodies and analyzed via confocal fluorescence microscopy after antibody staining. VHH6 antibodies were tested.
Figure 12:
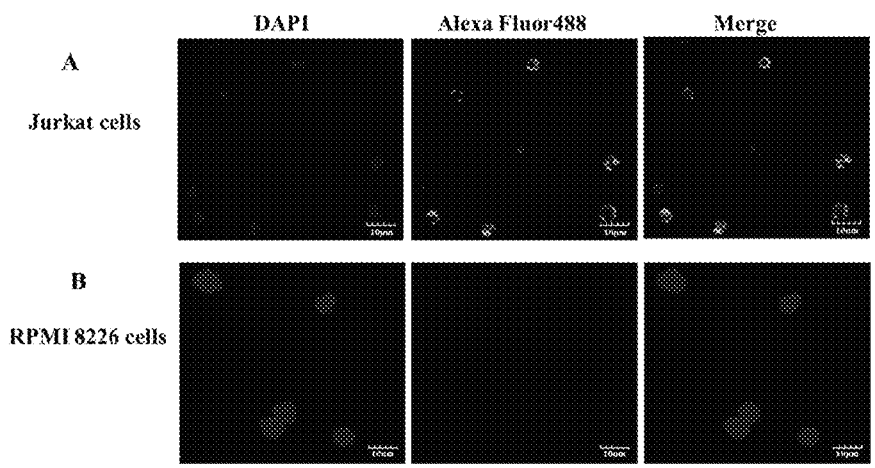
FIG. 12 shows confocal fluorescence microscopy images of Jurkat and RPMI8226 cells stained via the obtained high-purity VHH6 nanobody. Jurkat and RPMI8226 cells were incubated with VHH6 nanobodies, respectively, and then stained with DAPI and monoclonal antibody conjugated with Alexa Fluor 488.

FIG. 10, the CD7 protein plasmid (pcDNA3.1-CD7) was transfected into H460 cells and detected with flow cytometry using commercial PE labeled CD7 antibody. The transfection efficiency was 18.8%. Similarly, the screened nanobody (the antibody clone 6 of the present invention, i.e., clone VHH-6) was used in the immunofluorescence assay (FIG. 11) to analyze H460 cells transfected with pcDNA3.1-CD7 plasmid (FIG. 11). The percentage of the positive cells to total cells in the visual field was analyzed and the positive rate was about 20%, indicating that the effects of the antibodies of the present invention were similar to that of commercial antibodies. FIG. 12 showed that CD7 expression can be detected on the surface of Jurkat cells, and RPMI8226 was a negative control.

Example 8 Preparation of CD7 Nanobody Immunotoxins and Biological Activity

Figure 13:
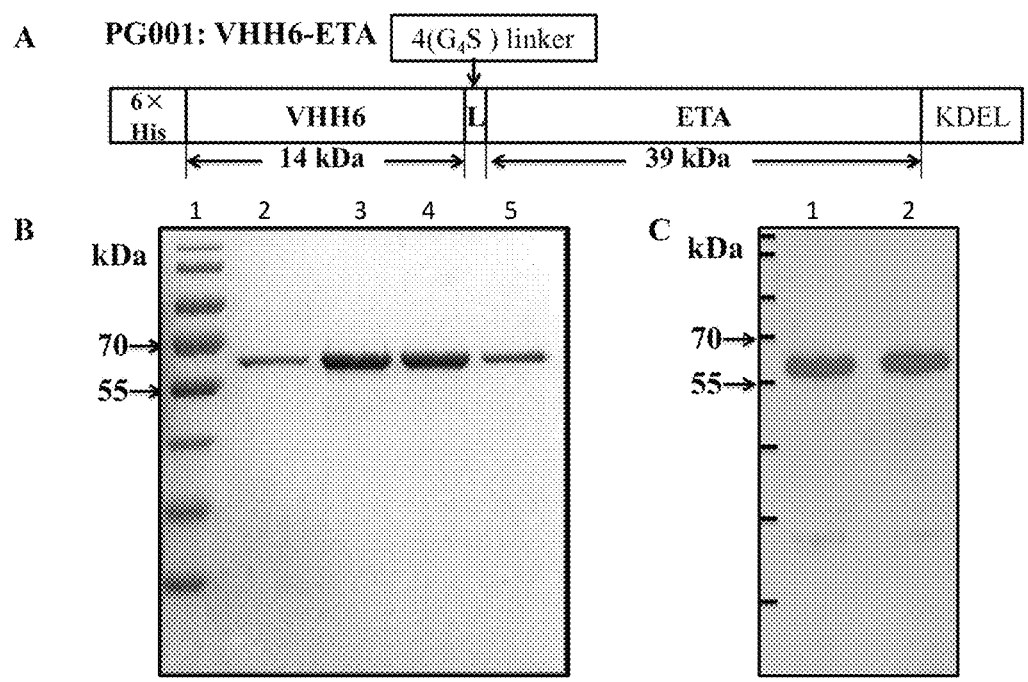
FIG. 13 shows construct and characterization of VHH-6-ETA, named PG001.
Figure 14:
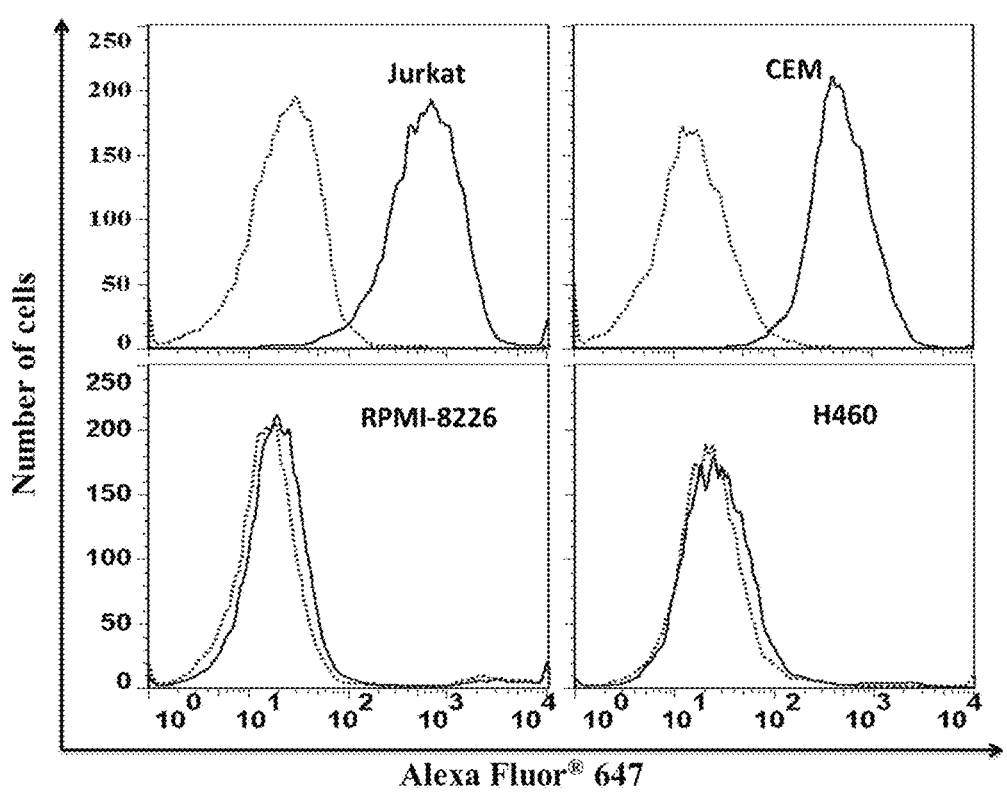
FIG. 14 shows results of flow cytometry assay of CD7-positive cell Jurkat, CD7-positive cell CEM, CD7-negative cell RPMI8226, and CD7-negative cell H460, which are simultaneously stained with the obtained high-purity conjugated toxin antibody PG001.

1. The Construction of Monovalent Nanobody Immunotoxin and the Analysis of its Affinity and Specificity The sequences of truncated body PE38 of the Pseudomonas exotoxin and the nanobody VHH-6 were codon-optimized and inserted into the vector pET28a. The HIS label was set at the N-terminal for subsequent purification. The REDLK (SEQ ID NO: 51)_sequence at C-terminal was replaced by the KDEL sequence (SEQ ID NO: 49) and the sequence structure was shown in FIG. 13A. The vector was transformed into *E. coli* BL21 (DE3). After the expression and affinity purification, the high purity Nanobody immunotoxin VHH-6-PE38 was obtained, named PG001 (FIGS. 13B and C). The results showed that 1 liter of *E. coli* produced about 10 mg of purified PG001. The analysis of the specificity of PG001 found that it could bind to CD7-positive cell lines Jurkat and CEM cells with high specifically, but not to CD7-negative cell lines RPMI8226 and H460 cells (FIG. 14).

The coding sequence information of the truncated body PE38 of Pseudomonas exotoxin was shown in SEQ ID NO: 44).

2. The Specific Toxicity of PG001 to CD7+T Lymphocyte Lines

Figure 15:
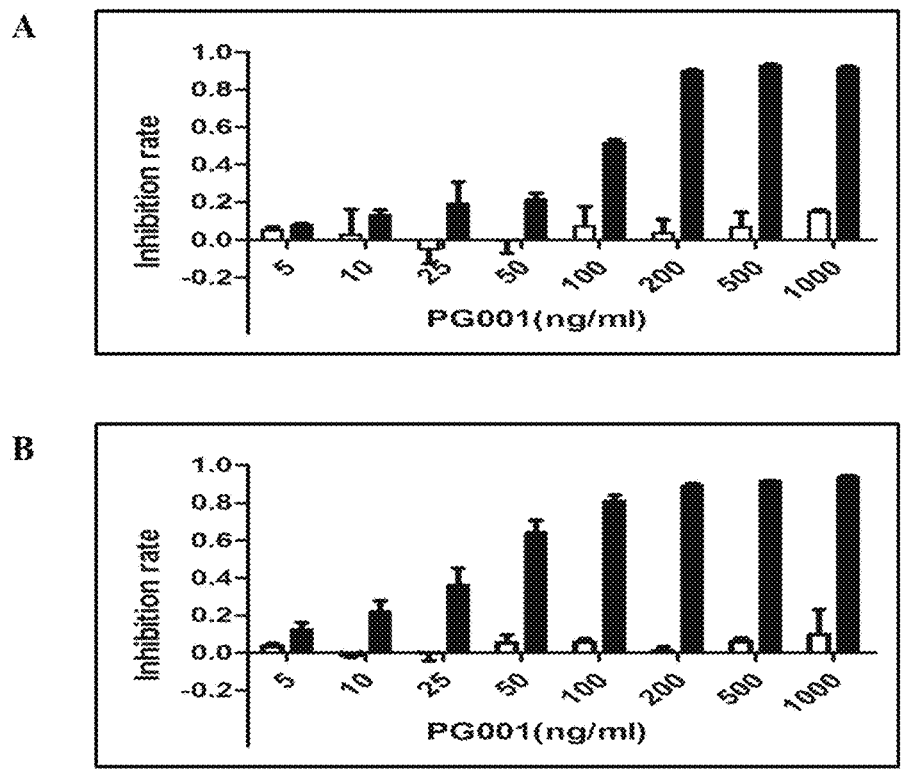
FIG. 15 shows cell-growth inhibition rates of PG001.
Figure 16:
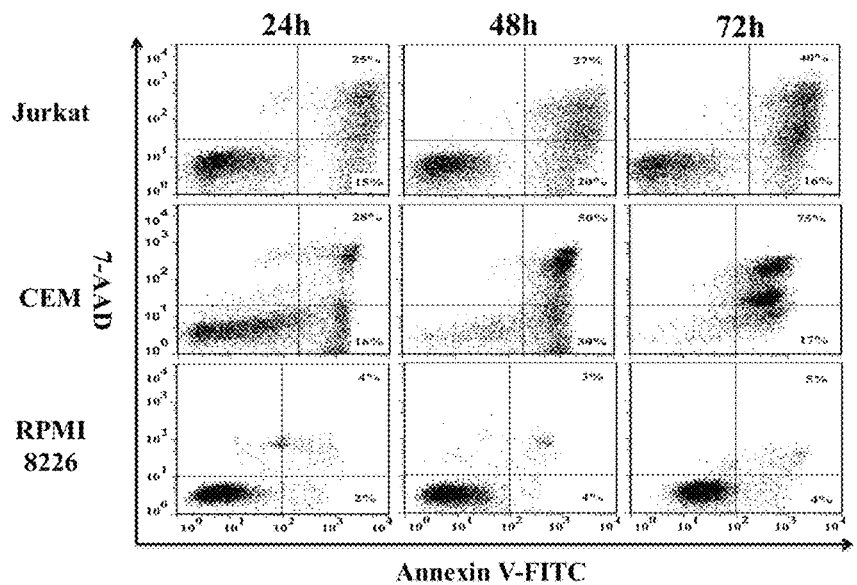
FIG. 16 shows apoptosis of Jurkat, CEM and RPMI8226 cells treated with 150 ng/ml of the obtained high purity PG001. Annexin V and 7-AAD were used for staining cells at 24 h, 48 h and 72 h. The cell population in the lower right quadrant represents early apoptotic cells (Annexin V positive and 7-AAD negative), and the cell population in the upper right quadrant represents dead cells (Annexin V and 7-AAD double positive). The data were obtained from three independent experiments.
Figure 17:
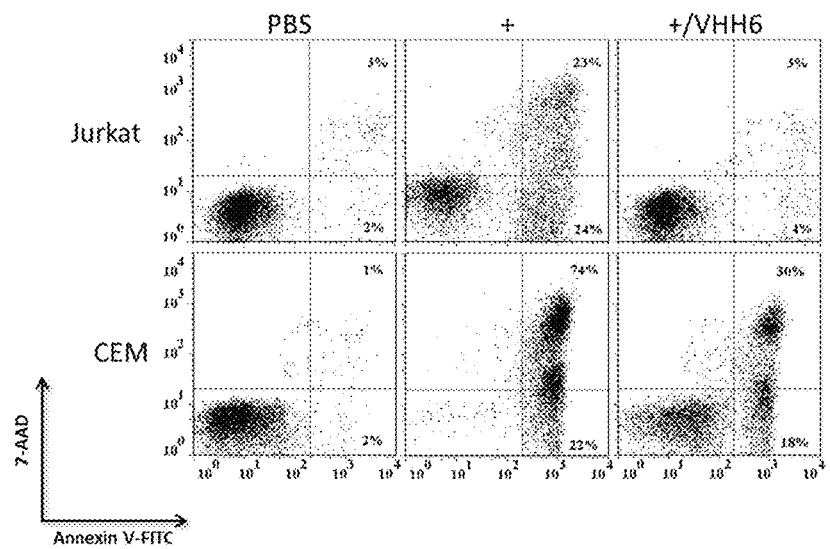
FIG. 17 shows cytotoxic effect of PG001 on CD7-positive Jurkat and CD7-positive CEM cells. "PBS" shows results of the CD7-positive Jurkat and CEM cells treated without PG001. "+" shows results of the CD7-positive Jurkat and CEM cells treated with a single dose of 150 ng/ml PG001 alone. "+/VHH6" shows results of the CD7-positive Jurkat and CEM cells treated with 150 ng/ml PG001 in the presence of 100-fold nanobody VHH6. After 48 hours, the treated cells were stained with Annexin V and 7-AAD. The cell population in the lower right quadrant represents early apoptotic cells (Annexin V positive and 7-AAD negative), and the cell population in the upper right quadrant represents dead cells (Annexin V and 7-AAD double positive). The data are obtained from three independent experiments.
Figure 18:
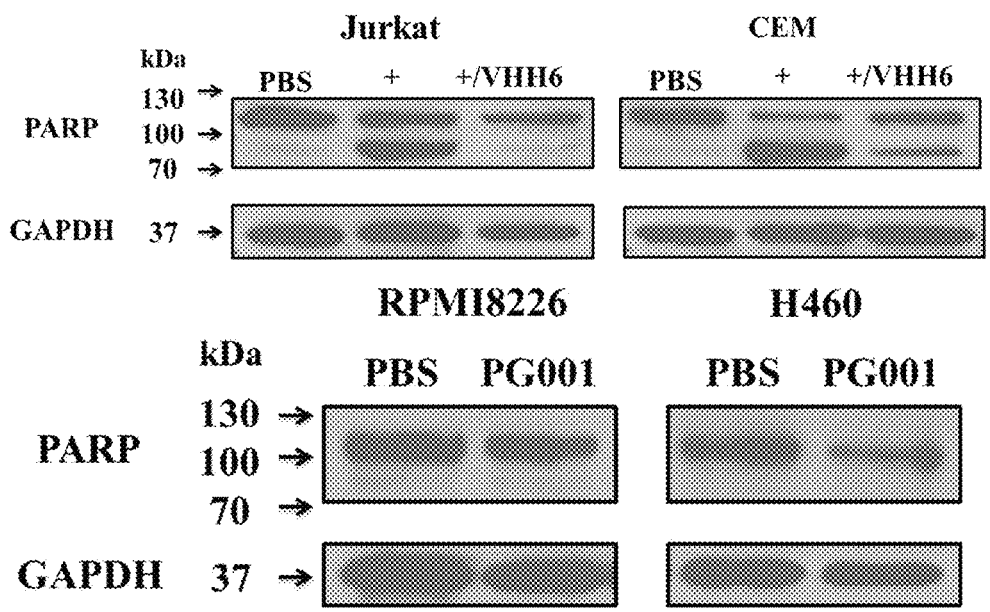
FIG. 18 shows PARP molecule cleavage by immunoblotting after Jurkat, CEM and RPMI8226, H460 cells were treated with the obtained high purity conjugated toxin antibody PG001 at 150 ng/ml PG001 for 48 hours. "PBS" represents treatment without PG001, "+" represents treatment with 150 ng/ml PG001 alone, and "+/VHH6" represents treatment with 150 ng/ml PG001 in the presence of 100 fold nanobody VHH6. Cleavage of the PARP molecule is a sign of cell apoptosis. When PG001 was incubated with CD7-positive Jurkat cells and CD7-positive CEM cells for 24 hours, PARP molecule-specific cleavage occurred, and the cleavage could be blocked by VHH6 nanobodies. When PG001 was incubated with CD7-negative RPMI8226 and CD7-negative H460 cells for 24 hours, PARP cleavage did not occur.

According to the toxic effect of PG001 determined by the WST-8 kit, PG001 was able to inhibit the proliferation of CEM (EC50≈0.5 nM) and Jurkat (EC50≈1.0 nM) at very low concentration, but not affect the growth of CD7-negative cells RPMI8226 and H460 (FIG. 15). In order to detect whether PG001-induced cell proliferation inhibition was induced by apoptosis, cells treated with PG001 were detected by Annexin V and 7-AAD staining. The results showed that the inhibition to the proliferation of two CD7-positive cells CEM and Jurkat was due to PG001-induced apoptosis time-dependently. However, it did not cause apoptosis in RPMI8226 cells at the same concentration (FIG. 16). At the same time, the cytotoxic effect of PG001 on Jurkat and CEM cells after treated for 48 hours was inhibited by incubation of parental antibodies at a 50-fold-concentration in advance (FIG. 17). In addition, PG001 treatment to Jurkat and CEM cells for 48 hours could induce PARP cleavage. It is well known that PARP cleavage was a marker of cell apoptosis, while RPMI8226 and H460 cells were treated by PG001 for 48 hours, PARP cleavage did not occur (FIG. 18). Thus, the above results indicated that the monovalent Nanobody immunotoxin PG001 is capable of specifically inducing apoptosis in the CD7-positive cell line under the nanomolar concentration, which is caused by receptor-mediated internalization of the Nanobody immunotoxin.

Figure 19:
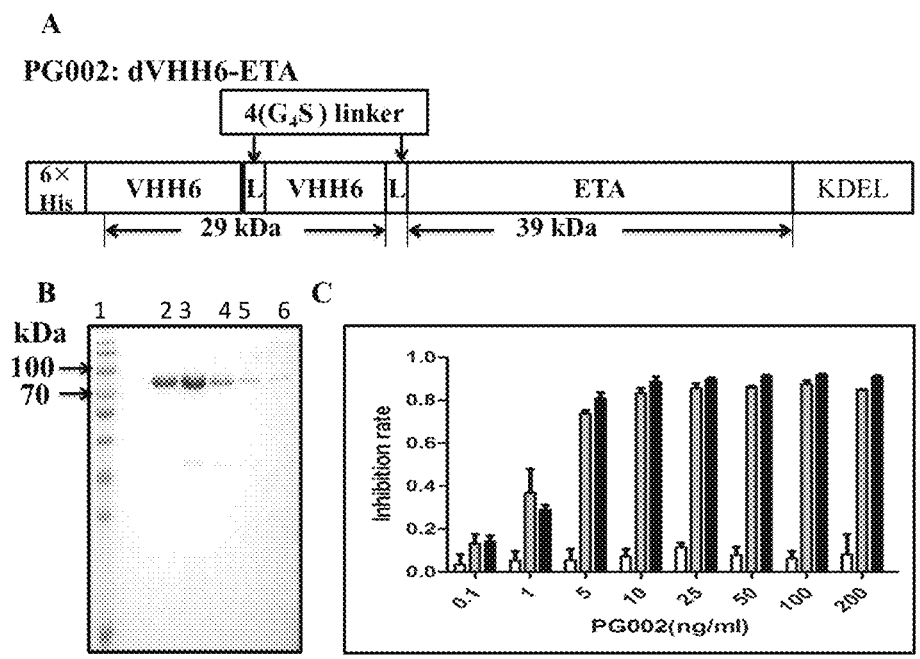
FIG. 19 shows preparation of a divalent nanobody immunotoxin PG002 and toxicological effects of the PG002.

3. The Construction of (VHH-6) 2-PE38 of Bivalent Nanobody Immunotoxin and its Specific Toxicity to CD7+T Lymphocyte Line In view of the superior selectivity and killing ability of PG001 and the short half-life of monovalent nano-antibody due to the smaller molecular weight of Nanobody and the relatively smaller size of the immunotoxin as constructed, the present inventors constructed the divalent nanobody to further improve the affinity between immunotoxins and target cells and to further reduce the dosage amounts of the immunotoxins. The sequence of truncated body PE38 of the Pseudomonas exotoxin and the divalent nanobody VHH-6 were codon-optimized and inserted into the vector pET28a. The HIS tag was set at the N-terminal for purification. The REDLK (SEQ ID NO: 51) sequence at C-terminal was replaced by the KDEL sequence (SEQ ID NO:49). The structure was as shown in FIG. 19A. The vector was transfected into *Escherichia coli* BL21. After expression and affinity purification, high purity divalent nanobody (VHH-6) 2-PE38 was obtained and named as PG002 (FIG. 19B). The inventors of the present invention found that 1 liter of *Escherichia coli* produced about 5 mg of purified PG002. And the toxic effect of PG002 was detected by WST-8 kit. The results showed that PG002 was able to strongly inhibit the proliferation of CD7 positive CEM (EC50=23 pM) and Jurkat (EC50=30 pM) cells at a lower concentration (pmol) but did not affect the growth of CD7-negative RPMI8226 cells (FIG. 19C).

4. The Anti-CEM Leukemia Cells Effect of PG001 in NOD/SCID Mice In Vivo

Figure 20:
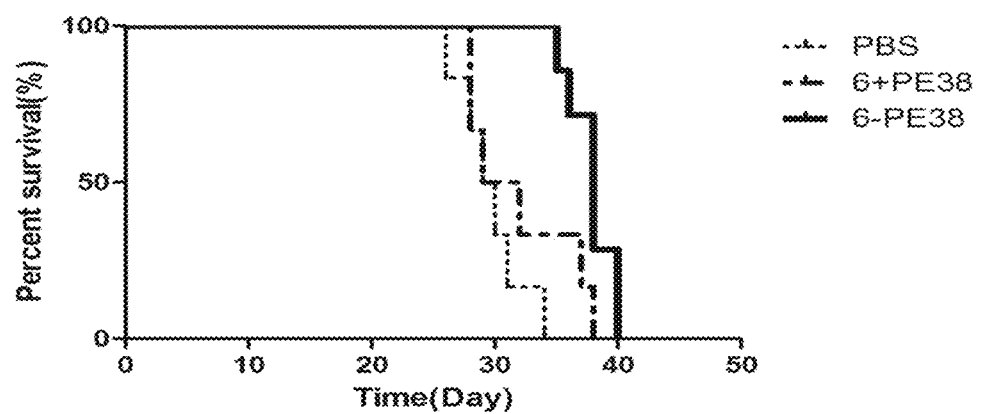
FIG. 20 shows effects of PG001 on anti-CEM leukemia cells in vivo by intravenously injecting NOD/SCID mice with the obtained high purity conjugated toxin antibody PG001. Curve "6-PE38" shows the percent survival of mouse group intravenously injected with the PG001, Curve "PBS" shows the percent survival of mouse group intravenously injected with PBS, and curve "6+PE38" shows the percent survival of mouse group intravenously injected with non-conjugated VHH-6 and PE38. The results show that the survival period of the mouse group injected with the PG001 is significantly longer than that of the control groups injected with PBS and VHH-6+PE38. The median survival time is 28.5 days for the group injected with PBS, 30.5 days for the group injected with VHH6+PE38, and 37 days for the group injected with PG001.

In order to detect the anti-leukemia potential of the Nanobody immunotoxin in animal models, the present inventors first evaluated the growth of anti-CEM leukemia cell lines in NOD/SCID mice using PG001 immunotoxins. On day 0, each mouse was injected with $2\times10^6$ CEM cells through the tail vein. After 5 days, 5 µg of the immunotoxin PG001 (or in the form of non-conjugated VHH-6 and PE38 (VHH-6+PE38)) was injected through the tail vein, injected every other day for three times total. The results showed that the survival period of the mice in the PG001 administration team was significantly longer than that of the control groups of PBS and VHH-6+PE38. The median survival time was 28.5 days in the PBS group and 37 days in the PG001 group. The experiments showed that disability in the hind legs and weight loss happened in the mice of administration group (FIG. 20).

DISCUSSION

The present inventors screened a specific CD7 nanobody from the camel and constructed the immunotoxins PG001 and PG002 against CD7 using the truncated body of Pseudomonas exotoxin and the monovalent and bivalent nanobody. These two toxins were able to induce apoptosis in acute leukemia cell lines in vitro efficiently and specifically at a concentration of nanomolar and picomolar, and induce the apoptosis of primary cells of T-ALL and T-AML patients specifically. Moreover, the monovalent Nanobody immunotoxin PG001 could effectively inhibit the growth of human leukemic cells transplanted into NOD/SCID mice.

The study had the following new findings:
a) The two Nanobody immunotoxins constructed by the inventors did not have Fc fragments as scFv fragments, thus the binding to non-target cells was greatly reduced.
b) The IC50 of the monovalent Nanobody immunotoxin PG001 of the present invention to the T-ALL cell lines (Jurkat and CEM) was at the nanomolar level, whereas the IC50 of the divalent Nanobody immunotoxin PG002 to the T-ALL cell lines (Jurkat and CEM) was at picomolar level. The killing effect was increased by about 30 folds.

c) Highly soluble, high-purity yields of these two immunotoxins as about 10 mg and 5 mg per liter of bacterial solution were obtained from prokaryotic expression of *E. coli* BL-21 (DE3) respectively. There were about 50 to 100 times improvement in yield compared to the prior art, which greatly reduced the production cost of such immunotoxins and had more clinical application value.

d) The inventors of the present invention analyzed the immunotoxins-treated cell staining by Annexin V and 7-AAD with flow cytometry and the cleavage of PARP molecules with Western blotting, indicating that the immunotoxins of the present inventors cause cell death by inducing apoptosis.

e) The Nanobody immunotoxins of the present invention could effectively kill T-ALL cell lines at low concentrations, and the divalent Nanobody immunotoxins constructed by the present invention could efficiently kill primary cells of T-ALL and T-AML patients at lower concentrations.

f) The present invention conducted an anti-human leukemia cell assay using monovalent Nanobody immunotoxin PG001 in NOD/SCID mice. The results showed that PG001 was able to significantly prolong the survival time of mice and it was the first time to research anti-Leukemia using Nanobody immunotoxin in vivo.

In the examples of the present invention, VHH-6 antibody clone are represented, and it has been experimentally verified that the other clones (such as VHH-10) provided by the present invention had biological activities similar to VHH-6 antibody clone.

In summary, the monovalent and bivalent nanobody CD7 immunotoxins are able to efficiently clear CD7-positive T-ALL cell lines and kill primary cells of T-ALL and T-AML patients in an antigen-specific manner at nanomolar and lower concentration.

All documents referred to in the present invention are incorporated by reference as if each reference is cited alone as a reference in the present application. In addition, it should be understood that after reading the teachings of the present invention described above, a skilled person in the art can make various changes or modifications of the invention, and these equivalent forms also fall into the scope as defined by the appended claims of the present application.

The invention claimed is:

1. An anti-human CD7 nanobody that is a VHH chain comprising framework regions (FRs) and complementarity determining regions (CDRs),
wherein the FRs include FR1, FR2, FR3, and FR4, and the FRs are selected from the following:
FR1 as shown in SEQ ID NO:13, FR2 as shown in SEQ ID NO:14, FR3 as shown in SEQ ID NO:15, FR4 as shown in SEQ ID NO:8;
FR1 as shown in SEQ ID NO:5, FR2 as shown in SEQ ID NO:6, FR3 as shown in SEQ ID NO:7, FR4 as shown in SEQ ID NO:8;
FR1 as shown in SEQ ID NO:5, FR2 as shown in SEQ ID NO:14, FR3 as shown in SEQ ID NO:16, FR4 as shown in SEQ ID NO:8;
FR1 as shown in SEQ ID NO:1, FR2 as shown in SEQ ID NO:2, FR3 as shown in SEQ ID NO:3, FR4 as shown in SEQ ID NO:4;
FR1 as shown in SEQ ID NO:1, FR2 as shown in SEQ ID NO:9, FR3 as shown in SEQ ID NO:3, FR4 as shown in SEQ ID NO:4; or
FR1 as shown in SEQ ID NO:5, FR2 as shown in SEQ ID NO:10, FR3 as shown in SEQ ID NO:11, FR4 as shown in SEQ ID NO:12, and
wherein the CDRs include CDR1, CDR2, and CDR3, the CDRs are selected from the following:
CDR1 as shown in SEQ ID NO:28, CDR2 as shown in SEQ ID NO:29, CDR3 as shown in SEQ ID NO:22;
CDR1 as shown in SEQ ID NO:20, CDR2 as shown in SEQ ID NO:21, CDR3 as shown in SEQ ID NO:22;
CDR1 as shown in SEQ ID NO:30, CDR2 as shown in SEQ ID NO:31, CDR3 as shown in SEQ ID NO:22;
CDR1 as shown in SEQ ID NO:17, CDR2 as shown in SEQ ID NO:18, CDR3 as shown in SEQ ID NO:19;
CDR1 as shown in SEQ ID NO:17, CDR2 as shown in SEQ ID NO:23, CDR3 as shown in SEQ ID NO:24; or
CDR1 as shown in SEQ ID NO:25, CDR2 as shown in SEQ ID NO:26, CDR3 as shown in SEQ ID NO:27.

2. The anti-human CD7 nanobody of claim 1, wherein the anti-human CD7 nanobody has an amino acid sequence as shown in SEQ ID NO:36, SEQ ID NO:33, SEQ ID NO:37, SEQ ID NO:32, SEQ ID NO:34, or SEQ ID NO:35.

3. The anti-human CD7 nanobody of claim 1,
wherein the FRs are selected from the following:
FR1 as shown in SEQ ID NO:13, FR2 as shown in SEQ ID NO:14, FR3 as shown in SEQ ID NO:15, FR4 as shown in SEQ ID NO:8;
FR1 as shown in SEQ ID NO:5, FR2 as shown in SEQ ID NO:6, FR3 as shown in SEQ ID NO:7, FR4 as shown in SEQ ID NO:8; or
FR1 as shown in SEQ ID NO:5, FR2 as shown in SEQ ID NO:14, FR3 as shown in SEQ ID NO:16, FR4 as shown in SEQ ID NO:8, and
wherein the CDRs are selected from the following:
CDR1 as shown in SEQ ID NO:28, CDR2 as shown in SEQ ID NO:29, CDR3 as shown in SEQ ID NO:22;
CDR1 as shown in SEQ ID NO:20, CDR2 as shown in SEQ ID NO:21, CDR3 as shown in SEQ ID NO:22; or
CDR1 as shown in SEQ ID NO:30, CDR2 as shown in SEQ ID NO:31, CDR3 as shown in SEQ ID NO:22.

4. The anti-human CD7 nanobody of claim 1,
wherein the FRs are FR1 as shown in SEQ ID NO:13, FR2 as shown in SEQ ID NO:14, FR3 as shown in SEQ ID NO:15, FR4 as shown in SEQ ID NO:8, and
wherein the CDRs are CDR1 as shown in SEQ ID NO:28, CDR2 as shown in SEQ ID NO:29, CDR3 as shown in SEQ ID NO:22.

5. The anti-human CD7 nanobody of claim 1,
wherein the FRs are FR1 as shown in SEQ ID NO:5, FR2 as shown in SEQ ID NO:6, FR3 as shown in SEQ ID NO:7, FR4 as shown in SEQ ID NO:8; and
the CDRs are CDR1 as shown in SEQ ID NO:20, CDR2 as shown in SEQ ID NO:21, CDR3 as shown in SEQ ID NO:22.

6. The anti-human CD7 nanobody of claim 1,
wherein FRs are FR1 as shown in SEQ ID NO:5, FR2 as shown in SEQ ID NO:14, FR3 as shown in SEQ ID NO:16, FR4 as shown in SEQ ID NO:8; and
the CDRs are CDR1 as shown in SEQ ID NO:30, CDR2 as shown in SEQ ID NO:31, CDR3 as shown in SEQ ID NO:22.

7. The anti-human CD7 nanobody of claim 1,
wherein the FRs are FR1 as shown in SEQ ID NO:1, FR2 as shown in SEQ ID NO:2, FR3 as shown in SEQ ID NO:3, FR4 as shown in SEQ ID NO:4, and
wherein the CDRs are CDR1 as shown in SEQ ID NO:17, CDR2 as shown in SEQ ID NO:18, CDR3 as shown in SEQ ID NO:19.

8. The anti-human CD7 nanobody of claim 1,
wherein the FRs are FR1 as shown in SEQ ID NO:1, FR2 as shown in SEQ ID NO:9, FR3 as shown in SEQ ID NO:3, FR4 as shown in SEQ ID NO:4, and
wherein the CDRs are CDR1 as shown in SEQ ID NO:17, CDR2 as shown in SEQ ID NO:23, CDR3 as shown in SEQ ID NO:24.

9. The anti-human CD7 nanobody of claim 1,
wherein the FRs are FR1 as shown in SEQ ID NO:5, FR2 as shown in SEQ ID NO:10, FR3 as shown in SEQ ID NO:11, FR4 as shown in SEQ ID NO:12, and
wherein the CDRs are CDR1 as shown in SEQ ID NO:25, CDR2 as shown in SEQ ID NO:26, CDR3 as shown in SEQ ID NO:27.

10. A pharmaceutical composition comprising:
(i) the anti-human CD7 nanobody of claim 1; and
(ii) a pharmaceutically acceptable carrier.

* * * * *